United States Patent
Yamazaki et al.

(10) Patent No.: US 8,107,158 B2
(45) Date of Patent: Jan. 31, 2012

(54) FLUORESCENT IMAGING DEVICE AND FLUORESCENT IMAGE ACQUIRING METHOD

(75) Inventors: Kenji Yamazaki, Sagamihara (JP); Nobuyuki Doguchi, Hino (JP); Shunji Takei, Hachioji (JP); Sakae Takehana, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/853,751

(22) Filed: Aug. 10, 2010

(65) Prior Publication Data

US 2011/0157340 A1    Jun. 30, 2011

Related U.S. Application Data

(63) Continuation of application No. PCT/JP2010/055888, filed on Mar. 31, 2010.

(30) Foreign Application Priority Data

Apr. 21, 2009    (JP) ................................. 2009-103254

(51) Int. Cl.
    *G02B 26/00*    (2006.01)
(52) U.S. Cl. .............. 359/292; 348/61; 356/73; 359/396
(58) Field of Classification Search .................... 348/61; 359/292, 396; 356/73
    See application file for complete search history.

(56) References Cited

U.S. PATENT DOCUMENTS

| | | | |
|---|---|---|---|
| 5,983,120 A * | 11/1999 | Groner et al. ............. | 600/310 |
| 6,422,994 B1 * | 7/2002 | Kaneko et al. ............ | 600/160 |
| 6,465,968 B1 | 10/2002 | Sendai | |
| 6,956,695 B2 * | 10/2005 | Tafas et al. .............. | 359/396 |
| 2004/0162492 A1 | 8/2004 | Kobayashi | |
| 2006/0247535 A1 | 11/2006 | Sendai | |

FOREIGN PATENT DOCUMENTS

| | | |
|---|---|---|
| EP | 1 097 670 A2 | 5/2001 |
| EP | 1 705 477 A2 | 9/2006 |
| EP | 2 105 082 A1 | 9/2009 |
| JP | 2001-128925 | 5/2001 |
| JP | 2003-061909 | 3/2003 |
| JP | 2004-248721 | 9/2004 |
| JP | 2005-342234 | 12/2005 |
| JP | 2005-348902 | 12/2005 |
| JP | 2006-141686 | 6/2006 |
| JP | 2006-192065 | 7/2006 |
| JP | 2006-263044 | 10/2006 |
| JP | 2007-020775 | 2/2007 |
| JP | 2007-215927 | 8/2007 |
| JP | 2008-086605 | 4/2008 |
| JP | 2008-173290 | 7/2008 |
| WO | WO 2008/088002 A1 | 7/2008 |

OTHER PUBLICATIONS

International Search Report dated Jun. 22, 2010.

* cited by examiner

*Primary Examiner* — Phuoc Nguyen
(74) *Attorney, Agent, or Firm* — Scully, Scott, Murphy & Presser, P.C.

(57) ABSTRACT

A fluorescent imaging device includes an irradiation section that irradiates an object to be examined with excitation light and reference light, an image pickup section that picks up a fluorescence image based on the excitation light and a reflected light image based on the reference light, a comparison section that compares relative intensity between the fluorescent image generated from the fluorescence image and the reflected light image generated from the reflected light image, and a selection section that selectively outputs one of the reflected light image and the fluorescent image based on the comparison result.

15 Claims, 19 Drawing Sheets

| IMAGE SIGNAL | BRIGHTNESS (%) | | |
|---|---|---|---|
| | NORMAL | HYPERPLASTIC | ADENOMA |
| G-Em (i,j) | 100 | 40 | 15 |
| B-Re (i,j) | 100 | 100 | 20 |
| B-Re (i,j) / G-Em (i,j) | 1 | 2.5 | 1.3 |
| Rout (i,j) | 100 | 100 | 15 |

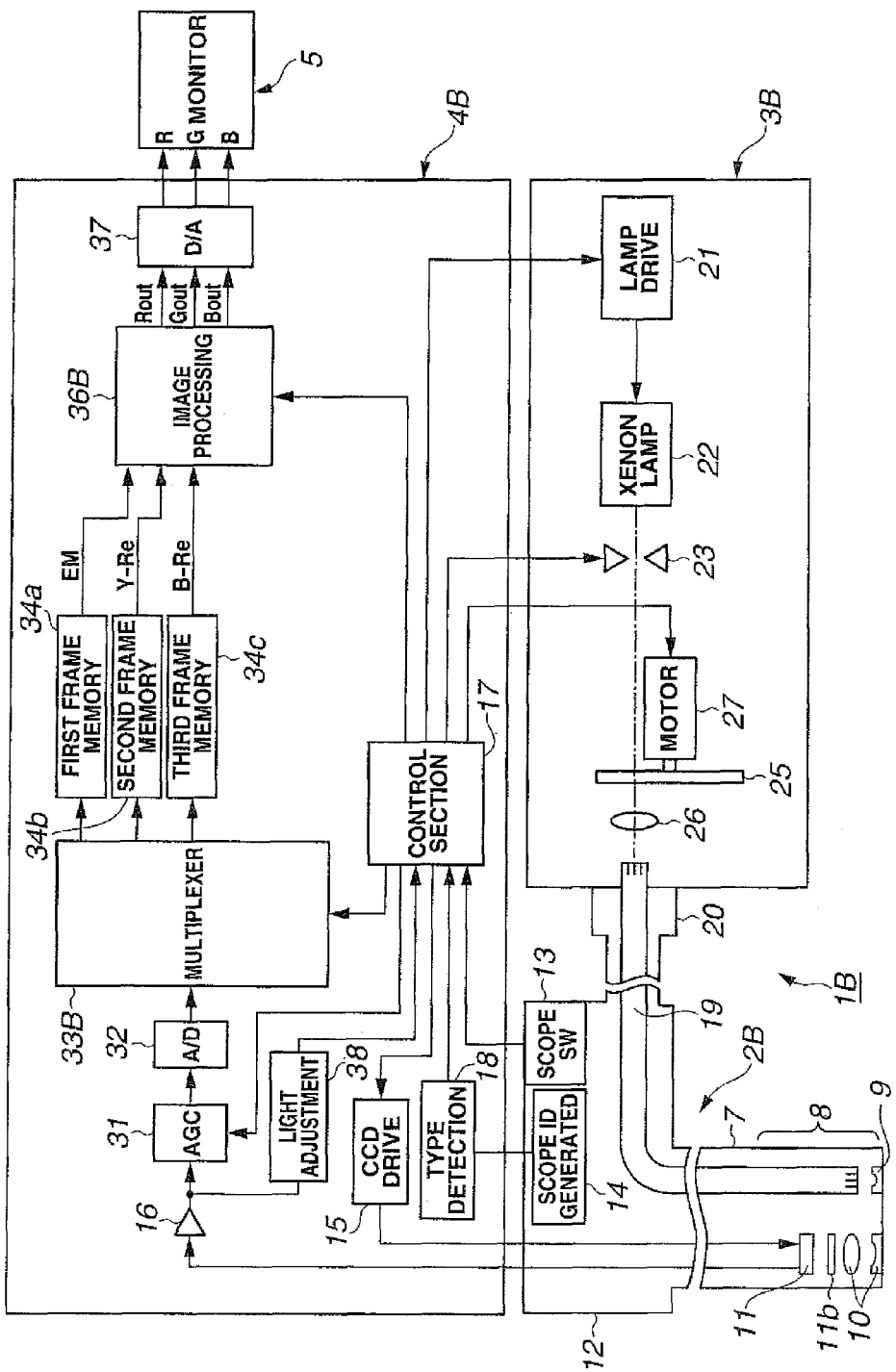

FLUORESCENT IMAGING DEVICE AND FLUORESCENT IMAGE ACQUIRING METHOD

CROSS REFERENCE TO RELATED APPLICATION

This application is a continuation application of PCT/JP2010/055888 filed on Mar. 31, 2010 and claims benefit of Japanese Application No. 2009-103254 filed in Japan on Apr. 21, 2009, the entire contents of which are incorporated herein by this reference.

BACKGROUND OF THE INVENTION

1. Field of the Invention

The present invention relates to a fluorescent imaging device that generates a fluorescent image and a fluorescent image acquiring method.

2. Description of the Related Art

In recent years, endoscopes are designed to be widely used for inspection and diagnosis of living tissue of diseased parts in the body cavity or the like. Furthermore, as disclosed, for example, in Japanese Patent Application Laid-Open Publication No. 2003-61909, there is a fluorescent imaging device that generates a fluorescent image to make it easier to diagnose whether living tissue is an abnormal (lesioned) region or a normal region by picking up an image using auto fluorescence emitted from the living tissue.

The fluorescent imaging device of the related art irradiates the living tissue with excitation light and reference light and generates a reference image as an image by returning light of the reference light through image pickup and a fluorescent image by fluorescence. Furthermore, this related art discloses a configuration which takes advantage of the fact that the intensity of a green light region of auto fluorescence in the lesioned region is lower than a normal region of the living body, and further uses a threshold of the luminance of the fluorescent image generated, and thereby extracts, colors and displays the lesioned region (tumor, cancer).

SUMMARY OF THE INVENTION

A fluorescent imaging device according to an embodiment of the present invention includes:

an irradiation section that irradiates an object to be examined with excitation light and reference light;

an image pickup section that picks up a fluorescence image based on the excitation light and a reflected light image including a first reflected light image of at least a predetermined wavelength region based on the reference light;

an image signal generating section that generates a plurality of image signals making up a diagnostic fluorescent image including an image signal of a fluorescent image corresponding to the fluorescence image, an image signal of the reflected light image including a first reflected light image corresponding to the first reflected light image from the reflected light image;

a comparison section that compares intensity of the fluorescent image and that of the first reflected light image multiplied by a predetermined value or relative intensity between the fluorescent image and the first reflected light image; and a selection section that selectively outputs one of the first reflected light image and the fluorescent image based on the comparison result by the comparison section as one image signal making up the diagnostic fluorescent image.

A fluorescent image acquiring method according to one embodiment of the present invention includes:

a first step of an image pickup section picking up a fluorescence image based on excitation light irradiated from an irradiation section onto an object to be examined and a reflected light image including at least a first reflected light image irradiated from the irradiation section onto the object to be examined based on reference light;

a second step of an image signal generating section generating a plurality of image signals making up a diagnostic fluorescent image including an image signal of a fluorescent image corresponding to the fluorescence image and an image signal of a reflected light image including a first reflected light image corresponding to the first reflected light image from the reflected light image;

a third step of a comparison section comparing intensity of the fluorescent image with that of the first reflected light image multiplied by a predetermined value or comparing relative intensity between the fluorescent image and the first reflected light image with a predetermined threshold; and a fourth step of a selection section selectively outputting any one of the first reflected light image and the fluorescent image based on the comparison result as one image signal making up the diagnostic image.

BRIEF DESCRIPTION OF THE DRAWINGS

FIG. 8 is a block diagram illustrating an overall configuration of a fluorescent imaging device according to a second embodiment of the present invention;

DETAILED DESCRIPTION OF THE PREFERRED EMBODIMENTS

Hereinafter, embodiments of the present invention will be described with reference to the accompanying drawings.

First Embodiment

Figure 1:
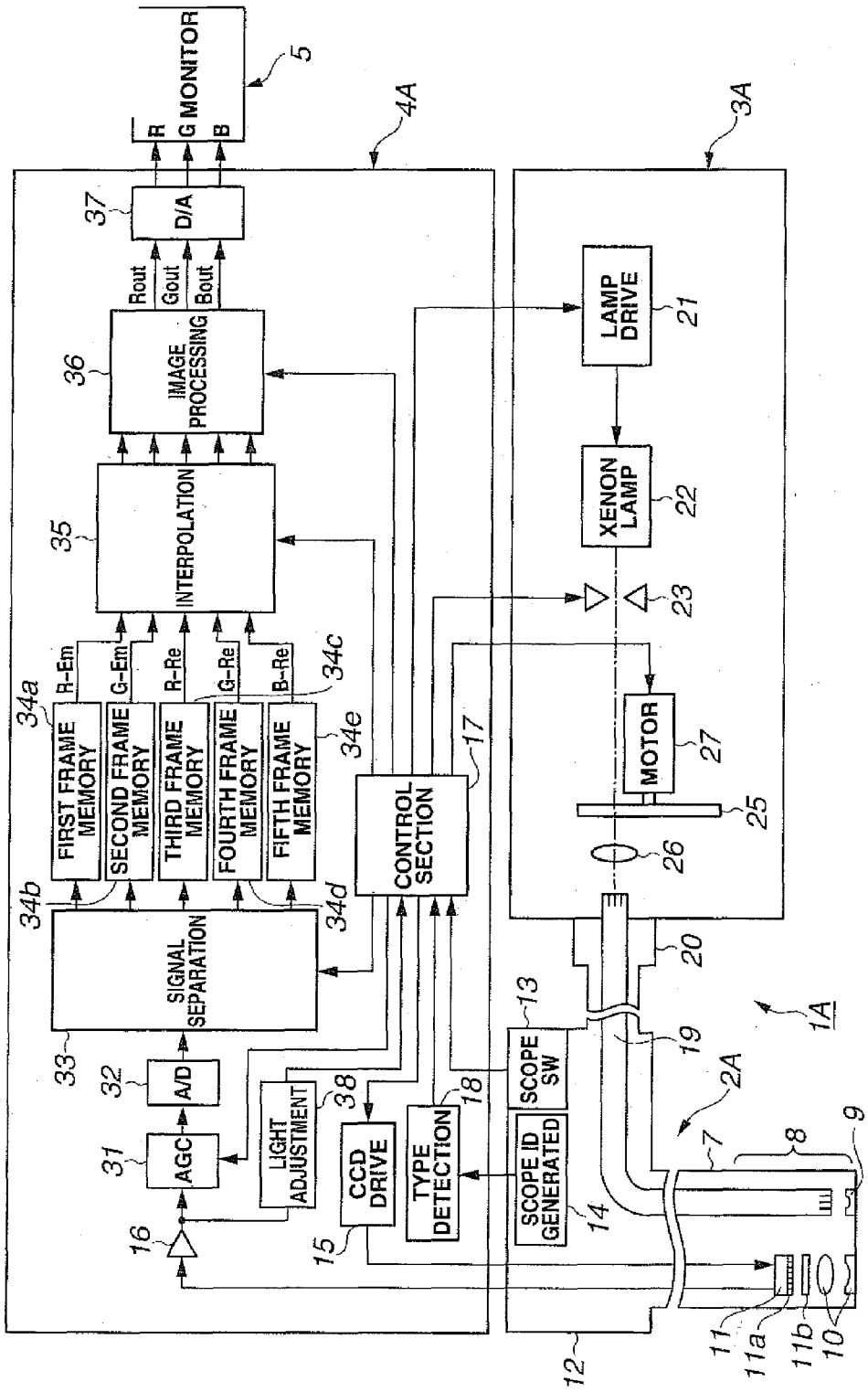
FIG. 1 is a block diagram illustrating an overall configuration of a fluorescent imaging device according to a first embodiment of the present invention.

As shown in FIG. 1, a fluorescent imaging device 1A according to the present embodiment is provided with an endoscope 2A for observing the interior of a living body as an object to be examined, a light source section 3A that sequentially irradiates one excitation light beam and one reference light beam made up of three narrow bands for making a fluorescence observation of the interior of the living body, a processor 4A including image signal generating means for performing signal processing on an image pickup signal picked up with fluorescence upon irradiation of the excitation light and an image pickup signal picked up with reflected light thereof under illuminating light upon irradiation of the reference light and generating a plurality of image signals including at least an image signal of fluorescence, and a color monitor (hereinafter, simply abbreviated as "monitor") 5 that displays images including the fluorescent image generated by the processor 4A in color.

The endoscope 2A has a flexible insertion portion 7 having an outside diameter that allows it to be inserted into the body cavity and a distal end portion 8 provided at a distal end of the insertion portion 7 is provided with an illumination lens 9 which forms irradiating means for spreading light supplied from the light source section 3A and irradiating the light onto the object to be examined, an objective lens 10 for forming an optical image of the object to be examined from returning light from the object to be examined and a CCD (charge coupled device) 11 as an image pickup device disposed at the image forming position.

Furthermore, a color filter 11a is attached in front of each pixel of the image pickup surface of the CCD 11 arranged in pixel units so as to separate light into colors red (R), green (G) and blue (B). Since the image pickup surface of the CCD 11 is provided with the optically color-separating color filters 11a, the CCD 11 outputs an image pickup signal color-separated for each pixel.

Furthermore, an excitation light cut filter 11b for cutting excitation light is disposed in front of the color filter 11a.

Furthermore, an operation section 12 provided at a rear end of the insertion portion 7 is provided with a scope switch 13 and a scope ID generating section 14 that stores specific ID information including at least the type of the endoscope 2A.

The CCD 11 which forms image pickup means is driven by a CCD drive signal outputted from a CCD drive circuit 15 provided in the processor 4A and outputs an image pickup signal which is an optical image picked up of the object to be examined to a preamplifier 16 provided in the processor 4A.

The scope switch 13 is provided with a plurality of switches such as a release switch which gives an instruction of recording an image corresponding to an optical image formed on the image pickup surface of the CCD 11 as a still image.

When the operator operates the scope switch 13, an operation signal based on the operation is outputted to a control section 17 provided in the processor 4A and the control section 17 performs control over each section of the fluorescent imaging device 1A based on the operation signal.

When the endoscope 2A is connected to the processor 4A, the scope ID generating section 14 outputs ID information of the connected endoscope 2A to a type detection circuit 18 provided in the processor 4A. Using the ID information of the endoscope 2A, the control section 17 performs various types of control corresponding to the CCD 11 used for the endoscope 2A.

A light guide fiber 19 made of quartz fiber or the like to guide light irradiated from the light source section 3A is inserted in the insertion portion 7.

One end of the light guide fiber 19 is configured to have a light source connector 20 detachably connected to the light source section 3A and the other end of the light guide fiber 19 is disposed in the vicinity of the illumination lens 9 as irradiating means provided at the distal end portion 8 of the insertion portion 7.

The light source section 3A is provided with a lamp drive circuit 21, for example, a xenon lamp 22 that is driven by the lamp drive circuit 21 so as to emit light and emits light of a wavelength band approximate to white color light, a light source diaphragm (simply referred to as "diaphragm") 23 provided in the irradiating light path of the xenon lamp 22 for adjusting light quantity emitted from the xenon lamp 22 by limiting the light quantity, a rotation filter 25 provided in the optical path of the xenon lamp 22 and a condenser lens 26 that condenses light that has passed through the rotation filter 25.

The diaphragm 23 is connected to the control section 17 of the processor 4A and the control section 17 adjusts the aperture of the diaphragm 23 based on a control signal and controls light quantity adjustment. Furthermore, the control section 17 controls the operation of the lamp drive circuit 21.

The above described rotation filter 25 is attached to the axis of rotation of a rotation motor (hereinafter, simply referred to as "motor") 27 that drives the rotation filter 25 to rotate.

The motor 27 has an encoder (not shown) attached to the axis of rotation or the like and the encoder outputs a detection signal corresponding to the rotation drive state of the rotation filter 25 to the control section 17 of the processor 4A. The control section 17 controls the rotation of the motor 27 so that the rotation speed is kept constant.

Figure 2:
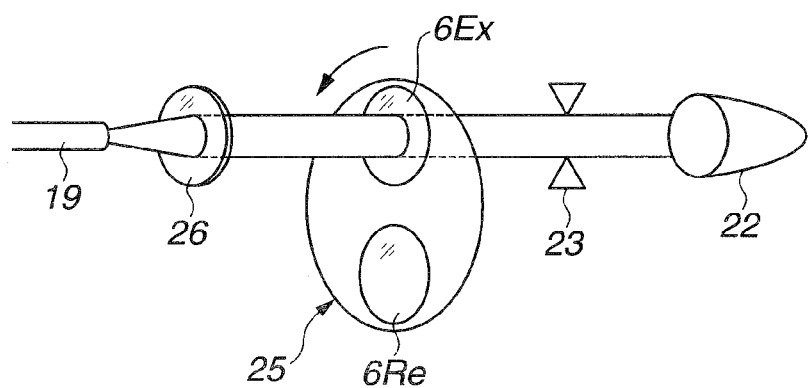
FIG. 2 is a diagram illustrating a configuration of a peripheral part of the rotation filter in the light source section.

FIG. 2 illustrates a configuration of a peripheral part of the rotation filter 25.

The rotation filter 25 has a circular shape, is provided with two openings in the circumferential direction thereof at equal angles and the two openings are provided with an excitation light filter 6Ex having transmission characteristics that allow excitation light to pass and a reference light filter 6Re having transmission characteristics that allow reference light to pass.

Figure 3:
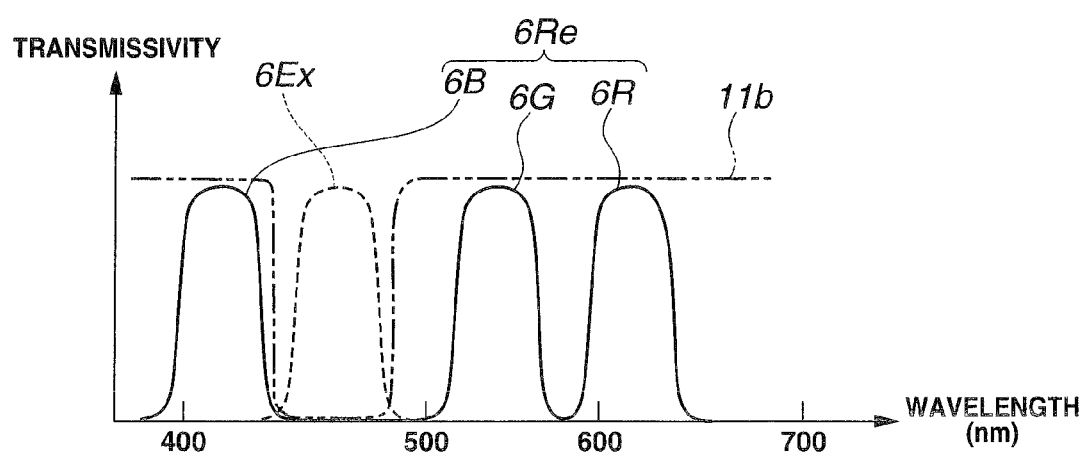
FIG. 3 is a diagram illustrating transmission characteristics of the excitation light filter or the like attached to the rotation filter in FIG. 2.

To be more specific, as illustrated with a dotted line in FIG. 3, the excitation light filter 6Ex demonstrates filter characteristics that allow to pass a wavelength band closer to a long wavelength in, for example, blue (B) color.

On the other hand, the reference light filter 6Re demonstrates filter characteristics with triplet peaks that allow to pass wavelengths of narrow band R, G and B in a narrow band as shown by a solid line in FIG. 3. FIG. 3 shows the R filter characteristic, G filter characteristic and B filter characteristic parts that allow to pass the R, G and B wavelength bands in the filter characteristics with triplet peaks as 6R, 6G and 6B respectively.

For the B filter characteristic 6B of narrow band, for example, a wavelength of 415 nm, which is selectively absorbed by hemoglobin, is set as its center wavelength. Furthermore, for the G filter characteristic 6G of narrow band and the R filter characteristic 6R of narrow band, their respective center wave lengths are set to 540 nm and 610 nm respectively.

Furthermore, as shown by a two-dot dashed line in FIG. 3, the excitation light cut filter 11b has a characteristic of selectively cutting a wavelength band of the excitation light filter 6Ex and has a characteristic of allowing to pass other wavelength bands.

As shown in FIG. 3, the present embodiment irradiates excitation light and reference light from the illumination lens 9 onto the object to be examined using light that has sequentially passed through the excitation light filter 6Ex and the reference light filter 6Re. The CCD 11, which forms image pickup means, then picks up an image of the object to be examined.

In this case, since the CCD 11 is simultaneous type image pickup means provided with the color filter 11a which separates light into colors R, G and B, when excitation light of a wavelength band of B is irradiated onto the object to be examined, the CCD 11 picks up a fluorescence image of auto fluorescence emitted through R and G from the object to be examined.

Furthermore, when light that has passed through the reference light filter 6Re provided with the R, G and B filter characteristics is irradiated onto the object to be examined, the CCD 11 picks up a reflected light image by reflected light reflected from the object to be examined.

The processor 4A in FIG. 1 is provided with the CCD drive circuit 15, the preamplifier 16, the control section 17, the type detection circuit 18, an AGC (auto gain control) circuit 31, an A/D (analog/digital) conversion circuit 32, a signal separation circuit 33, a first frame memory 34a, a second frame memory 34b, a third frame memory 34c, a fourth frame memory 34d, a fifth frame memory 34e, an interpolation circuit 35, an image processing circuit 36, a D/A (digital/analog) conversion circuit 37 and a light adjustment circuit (or brightness detection circuit) 38. An image pickup signal outputted from the CCD 11 is amplified by the preamplifier 16 and then inputted to the AGC circuit 31 and the light adjustment circuit 38.

The light adjustment circuit 38 detects average brightness of a picked-up image by the image pickup signal amplified by the preamplifier 16. Furthermore, the light adjustment circuit 38 compares the average brightness with a predetermined brightness target value.

The light adjustment circuit 38 then adjusts the aperture of the diaphragm 23 via the control section 17 by setting a signal corresponding to a difference from the target value as a light adjustment signal (brightness detection signal) for light adjustment.

When, for example, the brightness of the picked-up image is equal to or above a target value, the light adjustment circuit 38 outputs a light adjustment signal for reducing the aperture of the diaphragm 23, whereas when the brightness of the picked-up image is less than the target value, the light adjustment circuit 38 outputs a light adjustment signal for increasing the aperture of the diaphragm 23.

The image pickup signal outputted from the CCD 11 is amplified by the preamplifier 16, further amplified by the AGC circuit 31 to a predetermined level, and then converted from an analog signal to a digital signal by the A/D conversion circuit 32.

The image pickup signal converted to a digital signal passes through the signal separation circuit 33 that separates each color signal component color-separated by the color filter 11a from each image pickup signal and is converted to an image signal. The signal separation circuit 33 constitutes image signal generating means for generating a plurality of image signals for forming a diagnostic fluorescent image.

As will be described later, the diagnostic fluorescent image is made up of a plurality of (to be more specific, three) image signals and each image corresponding to each image signal in such a case corresponds to an image component of the diagnostic fluorescent image. In this case, each image corresponding to the diagnostic fluorescent image component is made up of at least one fluorescent image (including a case where the fluorescent image is mixed with the reflected light image) and the reflected light image.

The image signal separated and extracted by the signal separation circuit 33 is temporarily recorded in the first frame memory 34a, the second frame memory 34b, the third frame memory 34c, the fourth frame memory 34d and the fifth frame memory 34e which are image signal recording means.

The signal separation circuit 33 is formed of, for example, a multiplexer capable of high-speed switching and the multiplexer is switched by the control section 17 according to information from a ROM provided in the control section 17 that records information corresponding to the array of the color filter 11a.

In this case, for a period over which the image pickup signal of fluorescence is inputted to the multiplexer that forms the signal separation circuit 33 through excitation light, the control section 17 performs switching so that the image pickup signal is recorded in the first frame memory 34a at timing at which the image pickup signal of fluorescence of R is inputted, and an image signal R-Em of fluorescence of R is recorded in the first frame memory 34a.

In the present specification, I-Em (where I=R, G, B) denotes an image signal of the fluorescent image of a wavelength band of I. Likewise, J-Re (where J=R, G, B), which will be described later, denotes an image signal of the reflected light image of a wavelength band of J.

Furthermore, at timing at which the image pickup signal of fluorescence of G is inputted to the multiplexer, the control section 17 performs switching so that the image pickup signal is recorded in the second frame memory 34b and an image signal G-Em of fluorescence of G is recorded in the second frame memory 34b.

On the other hand, during a period over which the image pickup signal by reflected light through irradiation of reference light is inputted to the multiplexer that forms the signal separation circuit 33, the control section 17 performs switching so that the image pickup signal is recorded in the third frame memory 34c at timing at which the image pickup signal of the reflected light of R is inputted.

Furthermore, the control section 17 performs switching so that the image pickup signal is recorded in the fourth frame memory 34d at timing at which the image pickup signal by the reflected light of G is inputted, and performs switching so that the image pickup signal is recorded in the fifth frame memory 34e at timing at which the image pickup signal of reflected light of B is inputted.

The image signals R-Re, G-Re and B-Re of the reflected light beams of R, G and B are stored in the third frame memory 34c, the fourth frame memory 34d and the fifth frame memory 34e respectively.

The plurality of image signals recorded in the first frame memory 34a to the fifth frame memory 34e are synchronized with each other for a predetermined time period, then subjected to pixel interpolation by the interpolation circuit 35, inputted to the image processing circuit 36 as input image signals to be subjected to image processing, subjected to predetermined image signal processing as will be described below and a plurality of image signals making up a diagnostic fluorescent image are generated.

When the image processing circuit 36 carries out calculations between image signals (pixel signals) at the same pixel positions, the interpolation circuit 35 allows calculations to be performed by interpolating missing pixels with neighboring pixels or with an average value of surrounding pixels.

The interpolation circuit 35 performs processing of pixel interpolation under the control of the control section 17. The processing by the interpolation circuit 35 may also be performed by the image processing circuit 36. Furthermore, the interpolation circuit 35 may be provided between the signal separation circuit 33 and the first frame memory 34a to the fifth frame memory 34e.

In this case, the five interpolated image signals G-Em, B-Re, R-Em, G-Re and R-Re are stored in the first frame memory 34a to fifth frame memory 34e respectively. The control section 17 also controls the operation of the image processing circuit 36.

A plurality of image signals Rout, Gout, Bout generated through the image processing by the image processing circuit 36 are converted to an analog image signal by the D/A conversion circuit 37 and outputted to R, G and B channels of the monitor 5 respectively. The monitor 5 displays the plurality of (three) image signals Rout, Gout and Bout generated through the image processing by the image processing circuit 36 in color as diagnostic fluorescent images.

The CCD drive circuit 15 is controlled by the control section 17. The CCD drive circuit 15 applies CCD drive signals to the CCD 11 to read the image pickup signal of fluorescence and the image pickup signal of the reflected light from the CCD 11 at timing after irradiation of excitation light and timing after irradiation of reference light.

Furthermore, the control section 17 controls the CCD drive circuit 15 and the multiplexer of the signal separation circuit 33 based on a drive state signal outputted from the encoder of the motor 27.

Furthermore, the control section 17 controls the lamp drive circuit 21 and adjusts the light quantity or the like of light emitted by the xenon lamp 22.

Figure 4:
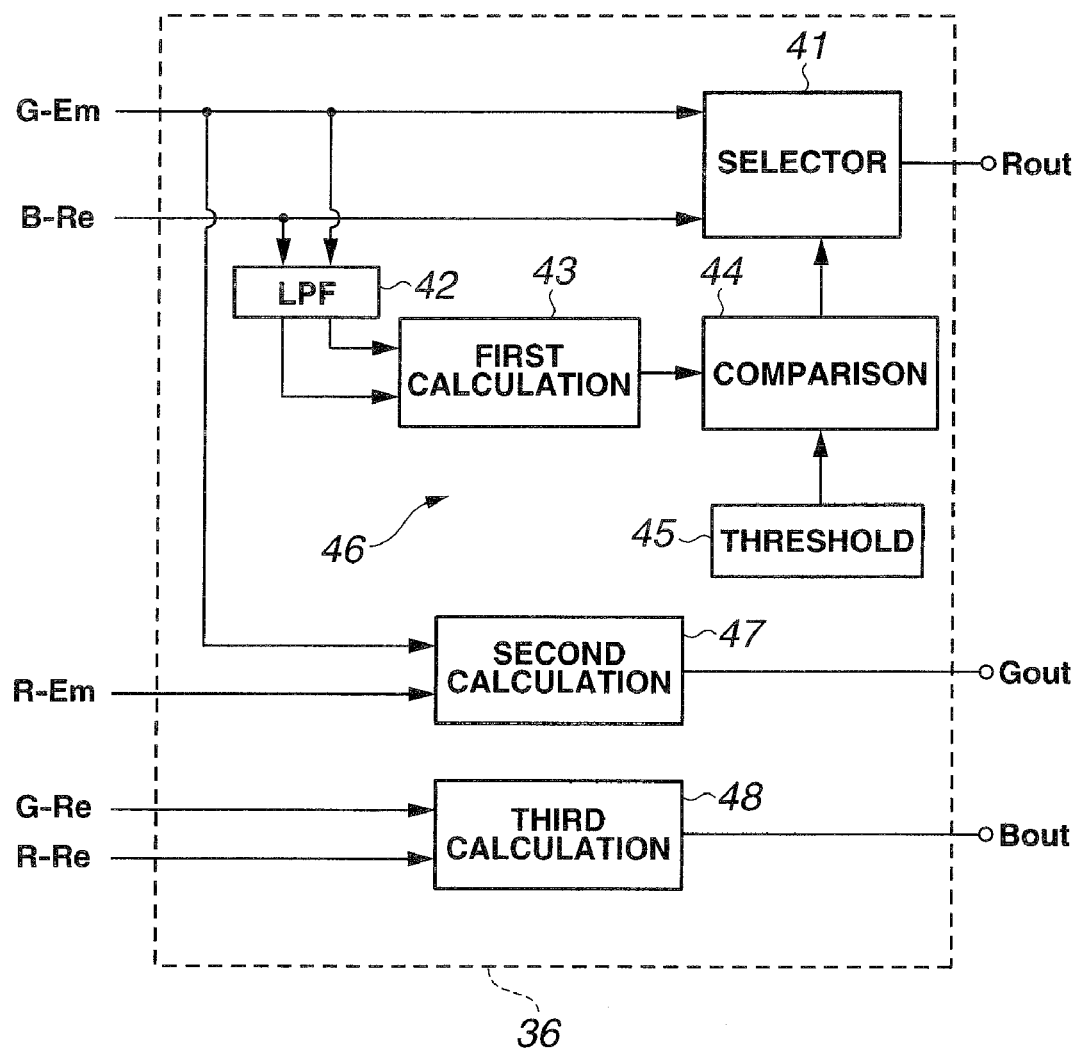
FIG. 4 is a block diagram illustrating a configuration of the image processing circuit.

FIG. 4 illustrates a configuration of the image processing circuit 36. The five image signals inputted to the image processing circuit 36 in FIG. 4 are G-Em, B-Re, R-Em, G-Re and R-Re and a plurality of image signals outputted from the image processing circuit 36 are expressed with Rout, Gout and Bout.

In the present specification, Rout, Gout and Bout denote image signals outputted to the R, G and B channels of the monitor 5 respectively as will also be described below and constitute a plurality of image signals making up a diagnostic fluorescent image.

As shown in FIG. 4, the image signal G-Em of fluorescence and image signal B-Re of reflected light of a specific wavelength band (also referred to as "first reflected light") are inputted to a selector 41 as selection means, pass through a low pass filter (LPF) 42 that performs pre-processing to reduce noise and are inputted to a first calculation circuit 43.

The first calculation circuit 43 performs a first calculation. To be more specific, $$B\text{-}Re(i,j)/G\text{-}Em(i,j) \tag{1}$$

is carried out as the first calculation. Here, (i, j) denotes two-dimensional coordinates in a two-dimensional image or a two-dimensional pixel position. Therefore, for example, B-Re (i, j) denotes a specific (first) reflected light image corresponding to the image signal B-Re of a specific wavelength band. Likewise, G-Em (i, j) denotes a fluorescent image corresponding to the image signal G-Em.

The other image signals also have similar meanings. As described above, the fluorescent image and the reflected light image have meanings of an image component of the diagnostic fluorescent image or a component image. As shown in Expression 1 above, the first calculation circuit 43 forms calculation means for calculating relative intensity between the specific reflected light image B-Re (i, j) and fluorescent image G-Em (i, j).

The calculated value resulting from a first calculation by the first calculation circuit 43 or calculated value B-Re (i, j)/G-Em (i, j) is compared by the comparison circuit 44 as comparison means with a predetermined threshold Vth from a threshold circuit 45. The predetermined threshold Vth is set to a value for identifying a normal region or a hyperplastic polyp as benign polyp and an adenoma as a lesioned region (roughly a value greater than 1). A comparison circuit 44 controls switching of the selector 41 as selection means according to the comparison result.

In this case, when the calculated value B-Re (i, j)/G-Em (i, j) resulting from the first calculation is greater than the threshold Vth, the comparison circuit 44 controls the switching so that the selector 41 selects the image B-Re (i, j) or the selector 41 selects the image G-Em (i, j) otherwise.

The image signal Rout of the image Rout(i, j) selectively outputted from the selector 41 is an image signal outputted to, for example, the R channel of the monitor 5 as a color signal of R.

The selector 41, the first calculation circuit 43, the comparison circuit 44 and the threshold circuit 45 form an image selection output circuit 46 that selectively outputs one of the fluorescent image and reflected light image of a specific wavelength band according to the relative intensity value between both. The image selection output circuit 46 outputs the selected image to the monitor 5 as one image signal making up the diagnostic fluorescent image suited to diagnosis as will be described later together with the other image signals.

As described above, since the monitor 5 displays the image B-Re (i, j) or image G-Em (i, j) according to the comparison result with the predetermined threshold Vth as the color component image of R, the color image displayed on the monitor 5 as a color display section has a different red color tone according to the result of comparison with the predetermined threshold Vth.

Furthermore, the fluorescence image signal G-Em and the image signal R-Em are inputted to a second calculation circuit 47 and the second calculation circuit 47 performs a second calculation. To be more specific, $$\{G\text{-}Em(i,j)+R\text{-}Em(i,j)+32\log(G\text{-}Em(i,j)/R\text{-}Em(i,j))\}/3 \quad (2)$$

is calculated as the second calculation. That is, the second calculation circuit 47 performs a calculation of dividing the sum of the intensities of the two fluorescence image signals and the intensity of a logarithmic ratio of both image signals by 3 for averaging.

The image signal Gout of the fluorescent image resulting from the second calculation by the second calculation circuit 47 becomes an image signal outputted to the G channel of the monitor 5.

Furthermore, the image signals G-Re and R-Re of the reflected light image are inputted to a third calculation circuit 48 and the third calculation circuit 48 performs a third calculation. To be more specific, $$\{G\text{-}Re(i,j)+R\text{-}Re(i,j)\}/2 \quad (3)$$

is calculated as the third calculation.

The image signal Bout of the reflected light image resulting from the third calculation by the third calculation circuit 48 becomes an image signal to be outputted to the B channel of the monitor 5.

Thus, the image processing circuit 36 according to the present embodiment does not simply compare (the image signal of) the fluorescent image with a threshold but compares a calculated value of calculating intensity relative to (the image signal of) the specific (first) reflected light image by the specific (first) reference light with the threshold Vth, selectively outputs an image signal of an image outputted to a specific channel (in this case, R channel) of the monitor 5 as a display apparatus that displays an image according to the comparison result and generates a diagnostic fluorescent image by including this image.

As the reflected light from specific reference light in this case, an image pickup signal is used which is picked up by reflected light generated through irradiation of reference light of a narrow band of B having a wavelength specifically absorbed by a hemoglobin-rich region of adenoma. The specific reference light is less absorbed in the hyperplastic polyp region as mucous membrane hypertrophy, and attenuation of the reflected light thereof is therefore small (substantially not attenuated when compared to the case of adenoma).

On the other hand, auto fluorescence attenuates in both the adenoma region and the hyperplastic polyp region as mucous membrane hypertrophy. In this case, the adenoma region has a higher degree of attenuation, but since the attenuation also depends on the intensity of excitation light, it is necessary to adjust the threshold in order to identify between both regions based only on the intensity of auto fluorescence. Thus, the present embodiment performs the aforementioned first calculation using the two characteristic features demonstrated by the adenoma and hyperplastic polyp. By performing the first calculation, a greater value is detected in the hyperplastic polyp region than the adenoma region. In this case, although the intensity of fluorescence depends on the intensity of excitation light, similar dependency is demonstrated in the case of reflected light, too, and it is thereby possible to sufficiently reduce influences of the intensity by dividing the specific reflected light image by the fluorescent image.

Through such calculations, the image selection output circuit 46 is formed which generates one image signal making up a high reliability diagnostic fluorescent image which more accurately discriminates or more easily identifies both regions.

The fluorescent imaging device 1A according to the present embodiment of such a configuration and operation of a fluorescent image acquiring method thereof will be described next with reference to FIG. 5. The fluorescent imaging device 1A is set to be ready for use as shown in FIG. 1.

To be more specific, the light source connector 20 of the endoscope 2A is connected to the light source section 3A and is also connected to the processor 4A so that a signal whose image is picked up by the endoscope 2A is inputted to the processor 4A. Furthermore, the processor 4A and the monitor 5 are connected so that a video signal of the processor 4A is outputted to the monitor 5. Thus, power is supplied to the fluorescent imaging device 1A so as to be set in an operation state. Then, the light source section 3A and the processor 4A are set in an operation state and the control section 17 controls operations of the respective sections of the light source section 3A and the processor 4A.

Figure 5:
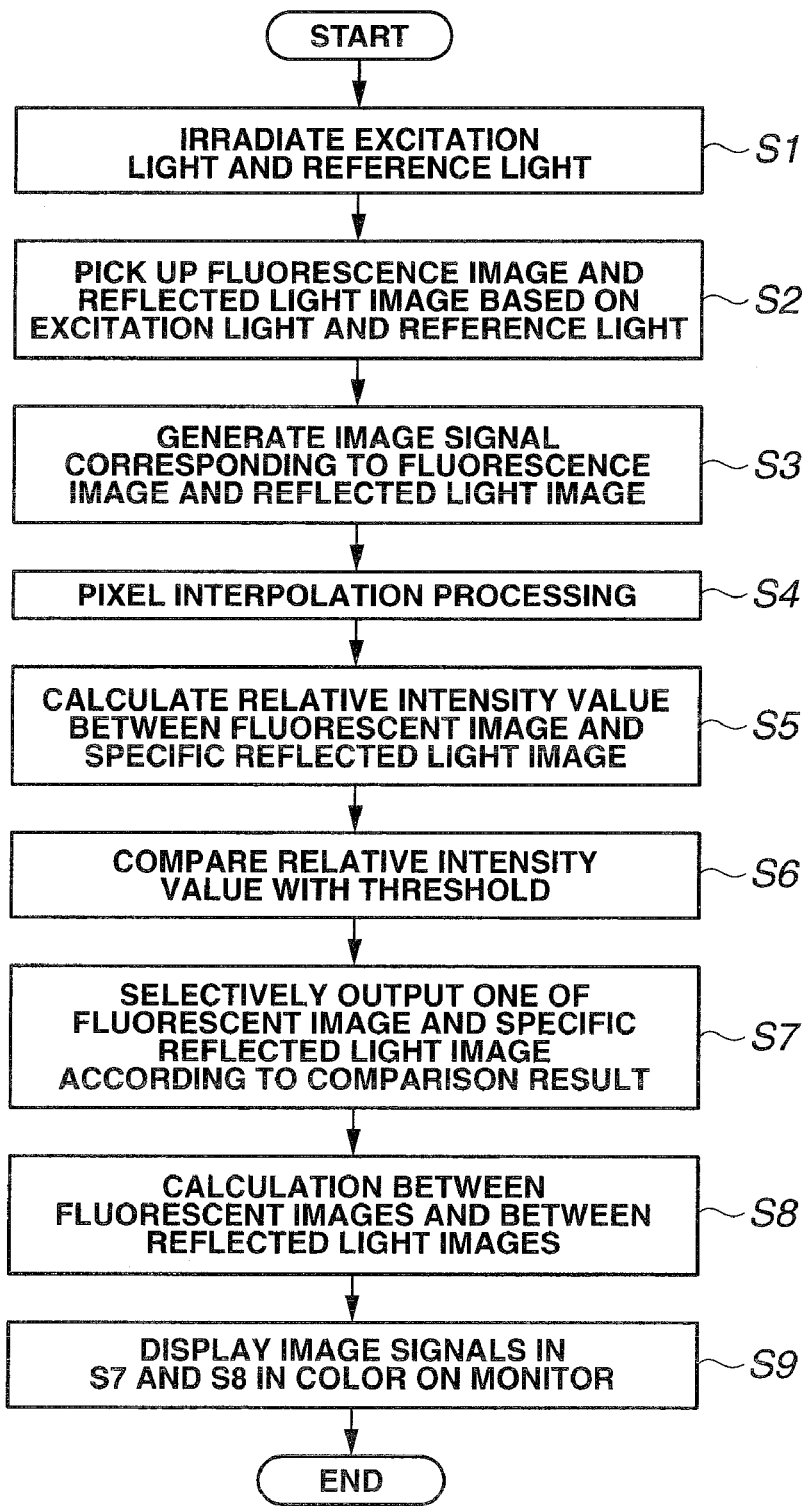
FIG. 5 is a flowchart illustrating a processing procedure of a fluorescent image acquiring method.

The light source section 3A sequentially (alternately) emits excitation light and reference light of R, G and B to the light guide fiber 19 of the endoscope 2A as shown in step S1 in FIG. 5 and the excitation light and the reference light are irradiated from the illumination lens 9 to the object to be examined via the light guide fiber 19.

As shown in step S2, the CCD 11 provided with the color filter 11a that forms the image pickup means of the endoscope 2A picks up a fluorescence image based on the excitation light and a reflected light image based on the reference light.

The image pickup signal captured by the CCD 11 is amplified by the preamplifier 16 of the processor 4A and the gain thereof is automatically adjusted by the AGC circuit 31 so as to have predetermined amplitude. The signal is then converted to a digital image pickup signal by the A/D conversion circuit 32 and inputted to the signal separation circuit 33.

During a period over which a fluorescence image pickup signal with which a fluorescence image is picked up is inputted (fluorescence signal period), the signal separation circuit 33 switches between the image pickup signal of fluorescence of R and the image pickup signal of fluorescence of G in pixel units according to the array of R and G of the color filter 11a and temporarily stores the image signal R-Em of fluorescence of R and the image signal G-Em of fluorescence of G in the first frame memory 34a and the second frame memory 34b respectively.

In this case, the addresses of the first frame memory 34a and the second frame memory 34b for storing the image signal R-Em of fluorescence of R and the image signal G-Em of fluorescence of G respectively are set to address values corresponding to the array of R and G of the color filter 11a.

Thus, those corresponding to the image signals of R and G color components in the fluorescence image color images optically separated into colors R, G and B and formed on the image pickup surface of the CCD 11 are stored in the first frame memory 34a and the second frame memory 34b.

That is, as shown in step S3, the image signals R-Em and G-Em of the fluorescent image corresponding to the fluorescence image formed on the image pickup surface of the CCD 11 are stored (generated) in the first frame memory 34a and the second frame memory 34b.

In substantially the same way as in the case of the fluorescence signal period, in a period (reflected light signal period) over which an image pickup signal of reflected light with which the reflected light image is picked up is inputted, the signal separation circuit 33 switches between the image pickup signal of reflected light of R, the image pickup signal of reflected light of G and the image pickup signal of reflected light of B in pixel units according to the array of R, G and B of the color filter 11a and temporarily stores the image pickup signals in the third frame memory 34c, the fourth frame memory 34d and the fifth frame memory 34e as image signals R-Re, G-Re and B-Re of reflected light of R, G and B.

In this case, the addresses of the third frame memory 34c to fifth frame memory 34e that store image signals R-Re, G-Re and B-Re of reflected light of R, G and B respectively are set to address values corresponding to the array of R, G and B of the color filter 11a.

Thus, those corresponding to the image signals of R-Re, G-Re, B-Re of color components of R, G and B in the color images of the reflected light images optically separated into colors R, G and B and formed on the image pickup surface of the CCD 11 are stored in the third frame memory 34c to fifth frame memory 34e.

That is, as shown in step S3, the third frame memory 34c to fifth frame memory 34e store the image signals R-Re, G-Re and B-Re of the reflected light images corresponding to the reflected light images formed on the image pickup surface of the CCD 11.

As shown in step S4, the five image signals R-Em, G-Em, R-Re, G-Re and B-Re stored in the first frame memory 34a to the fifth frame memory 34e are subjected to pixel interpolation by the interpolation circuit 35 and then inputted to the image processing circuit 36.

As shown in step S5, the image processing circuit 36 performs division processing as calculation processing of calculating a relative intensity value on (the image signal G-Em of) the fluorescent image whose noise has been reduced by the LPF 42 and (the image signal B-Re of) the reflected light image of a specific wavelength band through the first calculation circuit 43. The relative intensity value B-Re/G-Em calculated through the calculation processing in this step S5 is further subjected to comparison processing of comparing it with a predetermined threshold Vth in next step S6 by the comparison circuit 44.

Further, in next step S7, the comparison circuit 44 selectively outputs (the image signal G-Em of) the fluorescent image whose relative intensity value has been calculated by the first calculation circuit 43 according to the result of comparison with the predetermined threshold Vth and (the image signal B-Re of) the reflected light image of a specific wavelength band from the selector 41 as the image signal Rout of a predetermined image. The selectively outputted image signal Rout is outputted to, for example, the R channel of the monitor 5 as the display apparatus.

Furthermore, as shown in step S8, in the image processing circuit 36, the second calculation circuit 47 and the third calculation circuit 48 perform second calculation processing and third calculation processing of calculating an average value between the fluorescent images and between the reflected light images.

The two image signals Gout and Bout calculated by the second calculation circuit 47 and the third calculation circuit 48 are outputted to the G and B channels respectively.

As shown in next step S9, the image signal Rout from the image selection output circuit 46 including the first calculation circuit 43 in step S7 and the image signals Gout and Bout generated by the second calculation circuit 47 and the third calculation circuit 48 in step S8 are displayed in color on the display plane of the monitor 5 as the diagnostic fluorescent images to be used for diagnosis, in other words, as the endoscope fluorescent images.

The operator uses the diagnostic fluorescent images displayed in color on the monitor 5 for diagnosis. In this case, through image selection by the image selection output circuit 46, it is possible to display an adenoma and a hyperplastic polyp as mucous membrane hypertrophy on the monitor 5 in different color tones, and the operator can thereby easily make an accurate diagnosis. Therefore, the operator can perform diagnosis smoothly.

Figures 6, 7A:
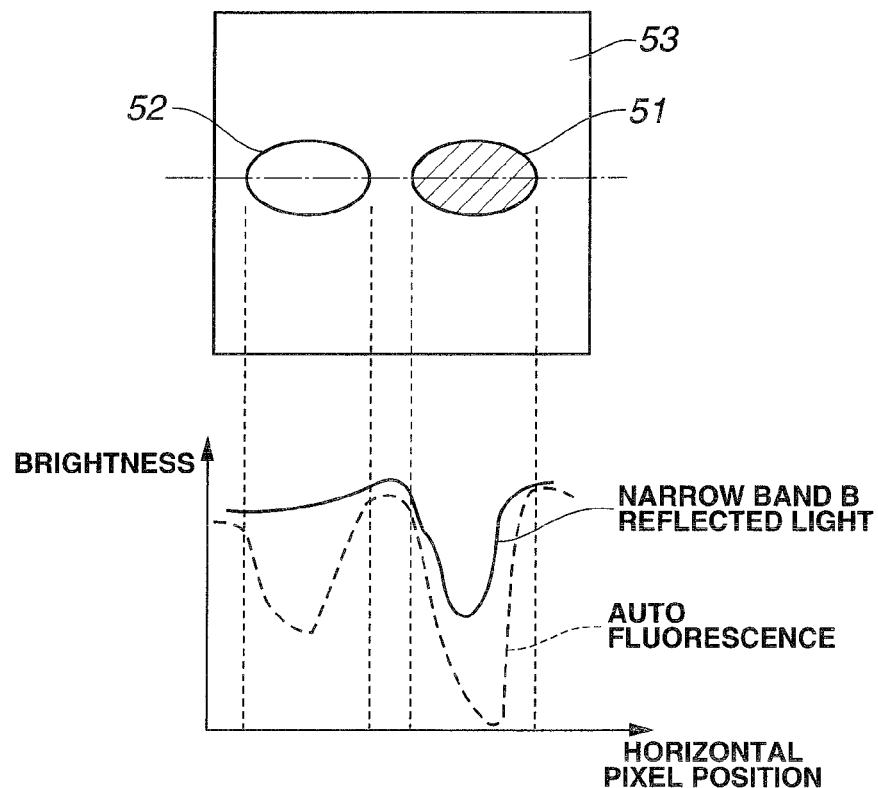
FIG. 6 is a diagram illustrating an image example for explanation of operation.
FIG. 7A is a table of numerical value examples for explanation of FIG. 6.

Next, the operation of the present embodiment in a case where a biological mucous membrane is observed as an object to be examined will be described more specifically. FIG. 6 illustrates a schematic view of an image of a biological mucous membrane in which an adenoma 51 is present with a hyperplastic polyp 52 in a mixed manner in a normal mucous membrane 53 and optical characteristic examples thereof.

To be more specific, an image of the biological mucous membrane in which the adenoma 51 is present with the hyperplastic polyp 52 in a mixed manner is shown in the upper part of FIG. 6 and characteristic examples of brightness (or luminance) at the horizontal coordinate positions along the horizontal line are shown therebelow.

Furthermore, as the characteristic examples of brightness in the lower part of FIG. 6, characteristics of brightness of the fluorescent image in the case of auto fluorescence and brightness of the reflected light image in the case of reference light of B of a narrow band are shown. In other words, this corresponds to the brightness of (the image signal G-Em of) the fluorescent image inputted to the first calculation circuit 43 in FIG. 4 and (the image signal B-Re of) the reflected light image of specific B.

As is clear from the characteristics in FIG. 6, the auto fluorescence considerably attenuates in a hemoglobin-rich region as in the case of the adenoma 51. Furthermore, the auto fluorescence also attenuates in the region of the hyperplastic polyp 52 though the degree of attenuation is smaller than that of the adenoma 51.

Furthermore, as shown in FIG. 6, the reflected light of B of a narrow band considerably attenuates in the hemoglobin-rich region as in the case of the adenoma 51. Thus, when the above described first calculation is performed, a rough evaluation in the region of the adenoma 51 results in a value approximate to 1.

By contrast, the reflected light of B of a narrow band hardly attenuates in the hyperplastic polyp 52 in substantially the same way as the normal biological mucous membrane. Thus, when a first calculation is performed, a rough evaluation in the region of the hyperplastic polyp 52 results in a value greater than 1.

Thus, when a value slightly greater than 1 is set as the threshold, a selectively outputted image is changed as described above based on the result of comparison with this threshold.

Thus, the image selectively outputted from the selector 41 becomes an image suited to discrimination or identification of the adenoma 51 and the hyperplastic polyp 52 in a more reliable state, that is, one characteristic image that forms a diagnostic fluorescent image. The present embodiment generates diagnostic fluorescent images including this image.

Thus, the present embodiment takes advantage of a difference in characteristics between the adenoma 51 and the hyperplastic polyp 52 with respect to auto fluorescence and reflected light of a specific wavelength as described above and thereby generates a diagnostic fluorescent image that makes it easier to discriminate or identify both (in other words, a diagnostic fluorescent image that facilitates an accurate diagnosis and provides high reliability).

By contrast, when the brightness of auto fluorescence is simply set as a threshold, it is necessary to drastically adjust the value of the threshold to discriminate or identify the adenoma 51 and the reliability thereof degrades.

FIG. 7A illustrates a calculation result by the first calculation circuit 43 assuming the brightness of the fluorescent image and the reflected light image as 100% in the portion of the normal mucous membrane 53 in the image in FIG. 6 and illustrates a table schematically expressing brightness as the adenoma 51 and hyperplastic polyp 52 in %. FIG. 7A then illustrates images selectively outputted from the selector 41 when the value of threshold Vth is set to, for example, on the order of 1.5 to 2.3.

As shown in FIG. 7A, the respective regions of the normal mucous membrane 53, the hyperplastic polyp 52 and the adenoma 51 differ in brightness of the fluorescent image of G, that is, G-Em (i, j) and brightness of reflected light image of B, that is, G-Em (i, j), and therefore a relative intensity value obtained by dividing the brightness of G-Em (i, j) by the brightness of G-Em (i, j) differs depending on the respective regions.

In this case, in the case of the related art that attempts to identify these regions based only on information of brightness of fluorescence, since the brightness of fluorescence obtained also depends on the intensity of excitation light, it is difficult to reliably identify the regions.

By contrast, in the present embodiment, the brightness of fluorescence depends on the intensity of excitation light as in the case of the related art, but since the dependency also has a similar tendency with reflected light, the influence thereof can be sufficiently reduced by calculating the brightness of fluorescence as a relative intensity value as described above. Moreover, the present embodiment sets the threshold Vth to a value with which it is easy to discriminate the hyperplastic polyp 52 from the adenoma 51 with respect to the above described relative intensity value.

Therefore, since the brightness is calculated with the above described relative intensity value, compared to the case where the relative intensity value is not adopted, this means that the value of the threshold Vth does not depend on the intensity of excitation light or the like and it is possible to discriminate or identify between the hyperplastic polyp 52 and the adenoma 51 with higher reliability.

An image corresponding to the mucous membrane hypertrophy (hyperplastic polyp) as a normal region or the adenoma as a lesioned region is selected according to the threshold Vth, and therefore the monitor 5 displays the images in different color tones.

Thus, the present embodiment can generate diagnostic fluorescent images with higher reliability and the operator can more easily make an accurate diagnose of the lesioned region.

The first calculation circuit 43 according to the aforementioned first embodiment is designed to calculate the relative intensity according to Expression 1, but a calculation expressed by the reciprocal of Expression 1, that is, Expression 1' may also be performed.

$$G\text{-}Em(i,j)/B\text{-}Re(i,j) \tag{1'}$$

The threshold of the threshold circuit 45 may be set to, for example, 1/Vth according to such a calculation. This modification example has substantially the same effects as those of the first embodiment.

As a second modification example of the image processing circuit 36 according to the first embodiment, the first calculation by the above described first calculation circuit 43 may be modified so as to calculate a contrast as follows.

To be more specific, the first calculation circuit 43 of the present modification example performs the following calculation as the first calculation.

$$|B\text{-}Re(i,j)-G\text{-}Em(i,j)|/|B\text{-}Re(i,j)+G\text{-}Em(i,j)| \tag{4}$$

|A| in Expression 4 means an absolute value of A. The threshold circuit 45 then sets a threshold corresponding to the calculation and the comparison circuit 44 compares the first calculation result with a threshold and switches the selector 41. G-Em or B-Re is selected and outputted according to a result of comparison with a threshold by the comparison circuit 44 in the same way as in the aforementioned first embodiment.

In the case of Expression 4, since the portion of numerator differs between both regions of the adenoma and the hyperplastic polyp, it is possible to discriminate or identify between the two using a threshold.

To put it in a rough way, the numerator in Expression 4 becomes a value approximate to 0 in the case of the tumor, whereas in the case of the hyperplastic polyp, the numerator is a value greater than 0. Thus, by setting an intermediate value between the two as the threshold, it is possible to accurately discriminate or identify between both regions according to the result of comparison with the threshold.

Furthermore, the present modification example also uses information of both the fluorescent image and the reflected light image, and can thereby discriminate or identify between the normal region and the lesioned region more reliably than in the case with only the fluorescent image, and display the images in different color tones according to the result. Thus, the operator can more easily make an accurate diagnosis.

Furthermore, according to the aforementioned first embodiment, when the value calculated by the first calculation circuit 43 is greater than the threshold Vth, the comparison circuit 44 selectively outputs the image signal B-Re of the reflected light image B-Re (i, j), but the comparison circuit 44 may also selectively output an average value of the image signal B-Re of the reflected light image B-Re (i, j) and the image signal G-Em of the fluorescent image G-Em (i, j).

By so doing, it is possible to more easily discriminate that the region is more likely to be a region of the hyperplastic polyp 52 which is different from an ordinary normal tissue.

The aforementioned first embodiment (and modification example) has described only the function of performing a fluorescence observation, but a configuration may also be adopted in which switching is performed so as to irradiate white color light, the color filter 11a performs color separation and normal simultaneous type image pickup and image processing, and make a normal observation to generate a normal color image for a visible wavelength region. This will be described later in connection with FIG. 25. Another embodiment, which will be described below, is also the same in that a configuration provided with a normal observation mode for making a normal observation may be adopted.

The aforementioned first embodiment adopts a configuration in which a value calculated by the first calculation circuit 43 in FIG. 4 is compared with a predetermined threshold as the calculation means for calculating relative intensity between a reflected light image and a fluorescent image. By contrast, as the following third modification example, selection means may be configured which selectively outputs one of the reflected light image and the fluorescent image based on an intensity comparison result using a predetermined value without comparing the relative intensity with a predetermined threshold.

Figure 7B:
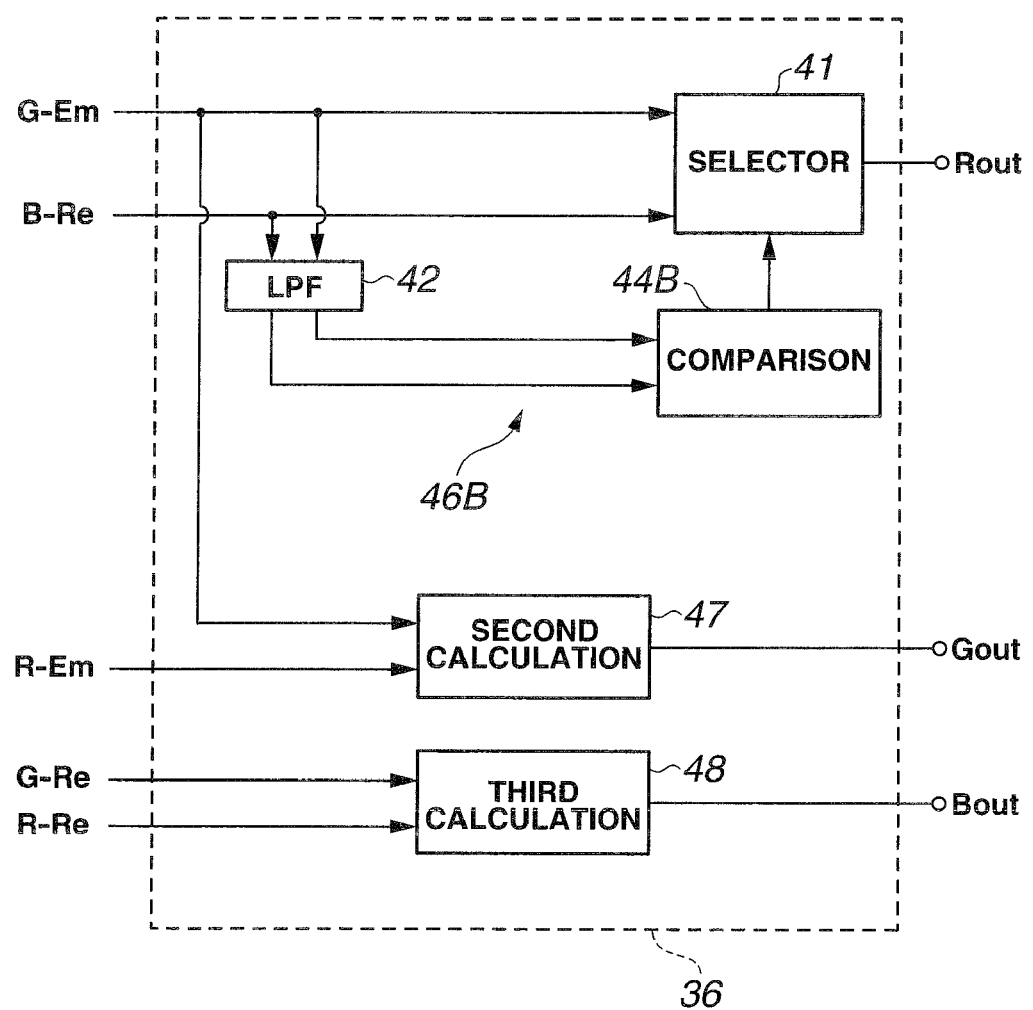
FIG. 7B is a block diagram illustrating a configuration of an image processing circuit according to a third modification example of the first embodiment.

FIG. 7B illustrates a configuration of an image selection output circuit 46B of the image processing circuit 36 of the present modification example. The image selection output circuit 46B adopts a configuration in which, for example, the first calculation circuit 43, the comparison circuit 44 and the threshold circuit 45 of the image selection output circuit 46 in FIG. 4 are changed to a comparison circuit 44B as comparison means.

An image signal G-Em of a fluorescent image G-Em (i, j) and an image signal B-Re of a reflected light image B-Re (i, j) are inputted to the comparison circuit 44B via the low pass filter 42.

The comparison circuit 44B forms comparison means for comparing the reflected light image B-Re (i, j) with the fluorescent image G-Em (i, j) multiplied by a predetermined value as shown in following Expression 4'. That is, the comparison circuit 44B performs a comparison to determine whether or not to satisfy:

$$B\text{-}Re(i,j) > k \times G\text{-}Em(i,j) \qquad (4')$$

The comparison circuit 44B controls, when the comparison result shows that Expression 4' is satisfied, the switching of the selector 41 in FIG. 7B and selectively outputs the image signal B-Re of the reflected light image B-Re (i, j).

On the other hand, when the comparison result shows that Expression 4' is not satisfied, the comparison circuit 44B controls the switching of the selector 41 in FIG. 7B and selectively outputs the image signal G-Em of the fluorescent image G-Em (i, j). Here, k is a predetermined value or a predetermined value multiplied by (pixel value average of B-Re (i,j)/(pixel value average of (G-Em (i,j)). The rest of the configuration is the same as that in the case of FIG. 4.

In the present modification example in such a configuration, the comparison circuit 44B controls the switching of the selector 41 in FIG. 7B according to the comparison result and selectively outputs the image signal B-Re of the reflected light image B-Re (i, j) and the image signal G-Em of the fluorescent image G-Em (i, j). The present modification example has substantially the same operation and effects as those of the first embodiment.

Here, Expression 4' may be transformed into the following Expression 4" so that the comparison circuit 44B performs a comparison in Expression 4".

$$B\text{-}Re(i,j)/G\text{-}Em(i,j) > k \qquad (4'')$$

In this case, the comparison circuit 44B compares the relative intensity between both images with k.

The left side of Expression 4" corresponds to Expression 1 and when k in the right side of Expression 4" is set in the threshold Vth, the processing contents correspond to those of the first calculation by the first calculation circuit 43 of calculating relative intensity according to the aforementioned first embodiment and making a comparison with a threshold by the comparison circuit 44.

In other words, the processing by the comparison circuit 44B includes the functions of a calculation section that calculates relative intensity and a comparison section that compares relative intensity with a threshold. Furthermore, as for the processing procedure corresponding to that in FIG. 5 in this modification example, the comparison circuit 44B performs processing (that is, Expression 4") including both processing contents in step S5 and step S6 in FIG. 5.

Second Embodiment

Next, a second embodiment of the present invention will be described with reference to FIG. 8 to FIG. 11. FIG. 8 illustrates a configuration of a fluorescent imaging device 1B according to the second embodiment of the present invention. The fluorescent imaging device 1B is constructed of an endoscope 2B provided with a monochrome CCD 11, a frame sequential light source section 3B, a processor 4B and a monitor 5. The endoscope 2B is an endoscope provided with the CCD 11 that picks up images under a frame sequential scheme without including the color filter 11a in the endoscope 2A in FIG. 1.

Figure 9:
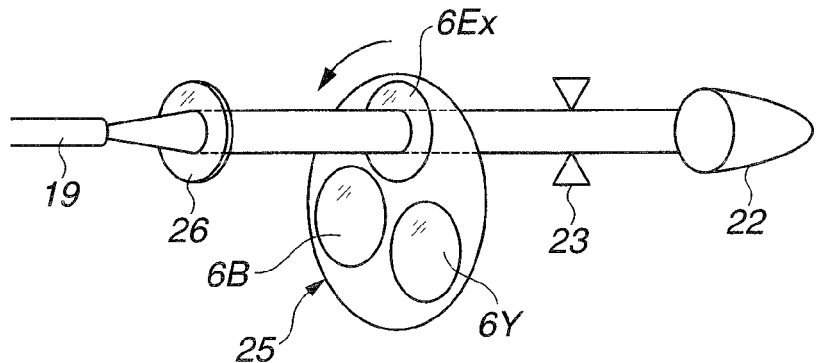
FIG. 9 is a diagram illustrating a configuration of a peripheral part of the rotation filter in the light source section.

Furthermore, the light source section 3B has the rotation filter 25 used for the light source section 3A in FIG. 1 provided with three filters as shown in FIG. 9.

FIG. 9 illustrates a configuration of a peripheral part of the rotation filter 25 of the present embodiment. The three filters shown in FIG. 9 are an excitation light filter 6Ex, a Y reference light filter 6Y that allows to pass a wavelength band of wideband yellow (Y), a narrow band B reference light filter 6B, and the excitation light filter 6Ex is the same as that of the first embodiment.

The first embodiment performs optical color separation through the color filter 11a on the image pickup means side, but since the present embodiment adopts the monochrome CCD 11, the two filters 6Y and 6B allowing to pass different wavelength bands are used to irradiate reference light.

Figure 10:
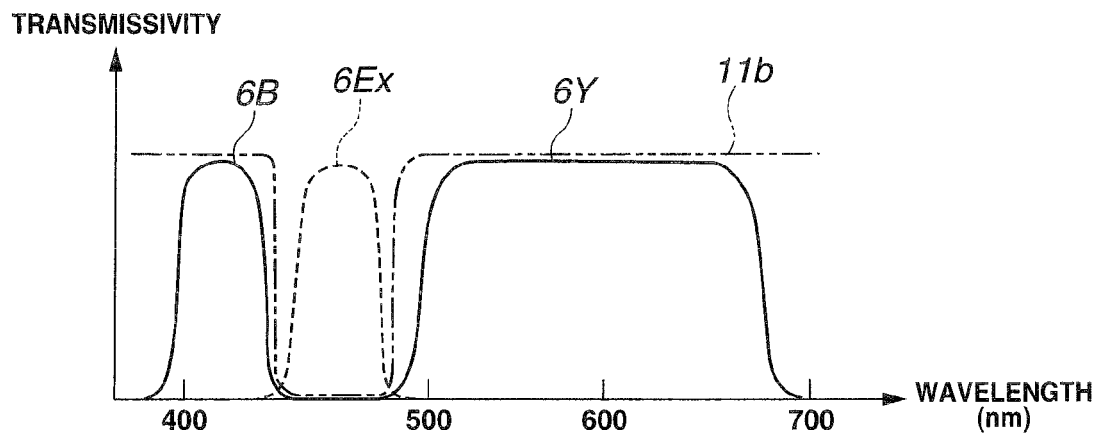
FIG. 10 is a diagram illustrating transmission characteristics of an excitation light filter or the like attached to the rotation filter in FIG. 9.

FIG. 10 illustrates transmission characteristics of these three filters 6Ex, 6Y and 6B. In this case, the filter 6B demonstrates filter characteristics of generating B light of the narrow band described in the first embodiment. The filter 6Y has characteristics of allowing to pass light of a wideband from the wavelength of G to the wavelength of R. The excitation light cut filter 11b is also disposed in front of the CCD 11 in the present embodiment in the same way as in the first embodiment.

This light source section 3B frame sequentially generates excitation light, Y light of a wideband (that is, G and R light) as reference light and B light of a narrow band. Through the irradiation of the excitation light, Y light of a wideband as reference light and B light of a narrow band, the monochrome CCD 11 picks up a fluorescence image, reflected light image corresponding to the Y light (that is, reflected light image of G and R) as reference light and reflected light image of B corresponding to the B light, and outputs their respective image pickup signals.

Furthermore, since the CCD 11 generates three image pickup signals as described above, the processor 4B according to the present embodiment adopts a multiplexer 33B that sequentially switches between three image pickup signals in frame units instead of the signal separation circuit 33 in the processor 4A in FIG. 1A and converts the image pickup signals to image signals.

To be more specific, an image pickup signal of fluorescence of excitation light, image pickup signals of Y light and B light are stored in a first frame memory 34a, a second frame memory 34b and a third frame memory 34c as an image signal Em of fluorescence, image signals Y-Re and B-Re of reflected light respectively.

The image signals Em, Y-Re and B-Re read from these frame memories 34a to 34c are inputted to an image processing circuit 36B.

Since the present embodiment adopts the above described monochrome CCD 11 and frame sequentially picks up images, image pickup signals of reflected light images picked up by the CCD 11 can also be regarded as image signals. By contrast, image pickup signals of reflected light images picked up in the aforementioned first embodiment are further passed through the signal separation circuit 33 and image signals are generated.

Figure 11:
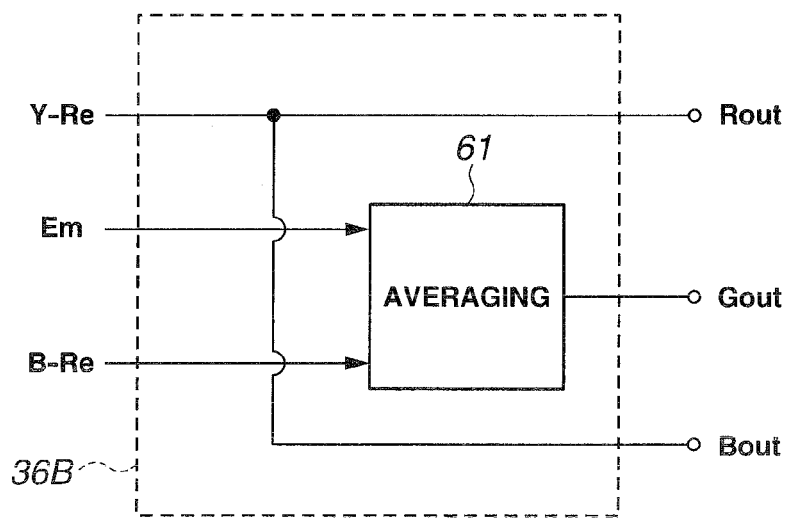
FIG. 11 is a block diagram illustrating a configuration of the image processing circuit.

FIG. 11 illustrates a configuration of the image processing circuit 36B according to the present embodiment. As will be described below, the image processing circuit 36B is provided with averaging processing means for averaging the fluorescence image and the specific reflected light image.

The image signal Y-Re of the reflected light image Y-Re (i, j) read from the second frame memory 34b is outputted as a red image signal Rout and also outputted as a blue image signal Bout. That is, $$Rout(i,j)=Y\text{-}Re(i,j) \quad (5)$$

$$Bout(i,j)=Y\text{-}Re(i,j) \quad (6)$$

As has been described in the first embodiment, (i, j) denotes coordinates or a pixel position of a two-dimensional image. Furthermore, the image signals Em of fluorescent images Em (i, j) and the image signal B-Re of the reflected light image B-Re (i, j) of a specific wavelength band read from the first frame memory 34a and the third frame memory 34c respectively are inputted to the averaging circuit 61, the two values are added up and the addition result is divided by 2 to obtain an average and the averaged image signal is outputted as a green image signal Gout. That is, $$Gout(i,j)=\{Em(i,j)+B\text{-}Re(i,j)\}/2 \quad (7)$$

The rest of the configuration is the same as that of the first embodiment.

An image signal of the fluorescent image brighter and easier to diagnose than the case with only the fluorescent image is generated by averaging the image signals as expressed by Expression 7.

In the present embodiment, the image processing circuit 36B outputs the image signals of the images in Expressions 5 to 7 to the R, G and B channels of the monitor 5 via the D/A conversion circuit 37 and diagnostic fluorescent images from the three image signals in Expressions 5 to 7 are displayed in color on the monitor 5.

The method of acquiring a diagnostic fluorescent image of the present embodiment will be described with reference to the flowchart of the first embodiment in FIG. 5 as follows.

As in step S1 in FIG. 5, excitation light and reference light are irradiated onto, for example, a biological mucous membrane as an object to be examined. To be more specific, excitation light that has passed through the excitation light filter 6Ex, reference light of Y (G and R) of a wideband and reference light of B of a narrow band are sequentially irradiated via the illumination lens 9.

As in step S2 in FIG. 5, a fluorescence image based on the excitation light and two reference light beams and two reflected light images are picked up by the CCD 11.

To be more specific, a fluorescence image of auto fluorescence emitted from the biological mucous membrane by the excitation light, a reflected light image by the reference light of Y (G and R) of a wideband and a specific reflected light image by the reference light of B of a narrow band are picked up and outputted from the CCD 11 as image pickup signals.

An image signal in step S3 is generated from the fluorescence image and image pickup signals of the two reflected light images in step S2. To be more specific, an image signal Em of the fluorescent image corresponding to the fluorescence image and image signals Y-Re and B-Re of the reflected light images corresponding to the two reflected light images are generated and stored in the first frame memory 34a to the first frame memory 34c.

Next, without performing step S4 in FIG. 5, the image processing circuit 36B performs averaging processing (instead of calculating a relative intensity value) on the fluorescent image and the specific reflected light image in correspondence with step S5. The image signal (Em+B-Re)/2 generated by this averaging processing is outputted to the G channel of the monitor 5.

This averaging processing is the processing in above described Expression 7 on the fluorescent image and the specific reflected light image. Next, without performing steps S6, S7 and S8 in FIG. 5, the image signal Y-Re of the reflected light image of a wideband is outputted to two R and B channels of the monitor 5 as shown in FIG. 11.

The three image signals outputted to these R, G and B channels are displayed in color on the monitor 5 as diagnostic fluorescent images.

The present embodiment adds up the fluorescent image and the specific reflected light image as shown in Expression 7, averages those images to generate an image signal and outputs the image signal to the monitor 5. By adding up and averaging both images, it is possible to realize lower contrast in the mucous membrane hypertrophy (hyperplastic polyp) region in the normal mucous membrane than when only the fluorescent image is outputted. Furthermore, it is possible to reduce noise, that is, an S/N more than when only the fluorescent image is outputted.

Therefore, the present embodiment has the following effects.

The contrast between the region of normal mucous membrane accompanied by mucous membrane hypertrophy and the region not accompanied by mucous membrane hypertrophy is high in the fluorescent image and low in the blue color reflected light image. Thus, the averaging processing can realize lower contrast than when only the fluorescent image is outputted. Furthermore, it is possible to reduce more noise than when only the fluorescent image is outputted.

Furthermore, by adopting the configuration in which image pickup is performed with reflected light of yellow color reference light, it is possible to reproduce mucous membrane information based on reference light in red color and green color and realize illumination corresponding to four bands of reference light in red color, green color, blue color and excitation light while maintaining irradiating light of three bands and an irradiation time thereof, and thereby also keep high the S/N of images obtained through irradiation of the respective bands.

The present embodiment performs averaging processing as described above. Therefore, it is possible to adjust intensity between the excitation light and reference light or adjust luminance between the fluorescence image and the reflected light image beforehand. In this case, the signal intensity between the fluorescence image and the reflected light image may be balanced using, for example, the normal mucous membrane as a reference.

As described above, the present embodiment adopts the configuration in which the averaged image signal is outputted to a specific channel of the monitor 5, but it may also be possible, as in the case of the first embodiment, to provide the selector 41, the comparison circuit 44, the threshold circuit 45 or the like, and switch between image signals to be selectively outputted from the selector 41 according to the result of comparison with a threshold by the comparison circuit.

When, for example, the luminance of an averaged image is compared to a preset threshold, if the luminance is equal to or below the threshold, the fluorescent image Em (i, j) or reflected light image B-Re (i, j) of B may be outputted.

Figure 12:
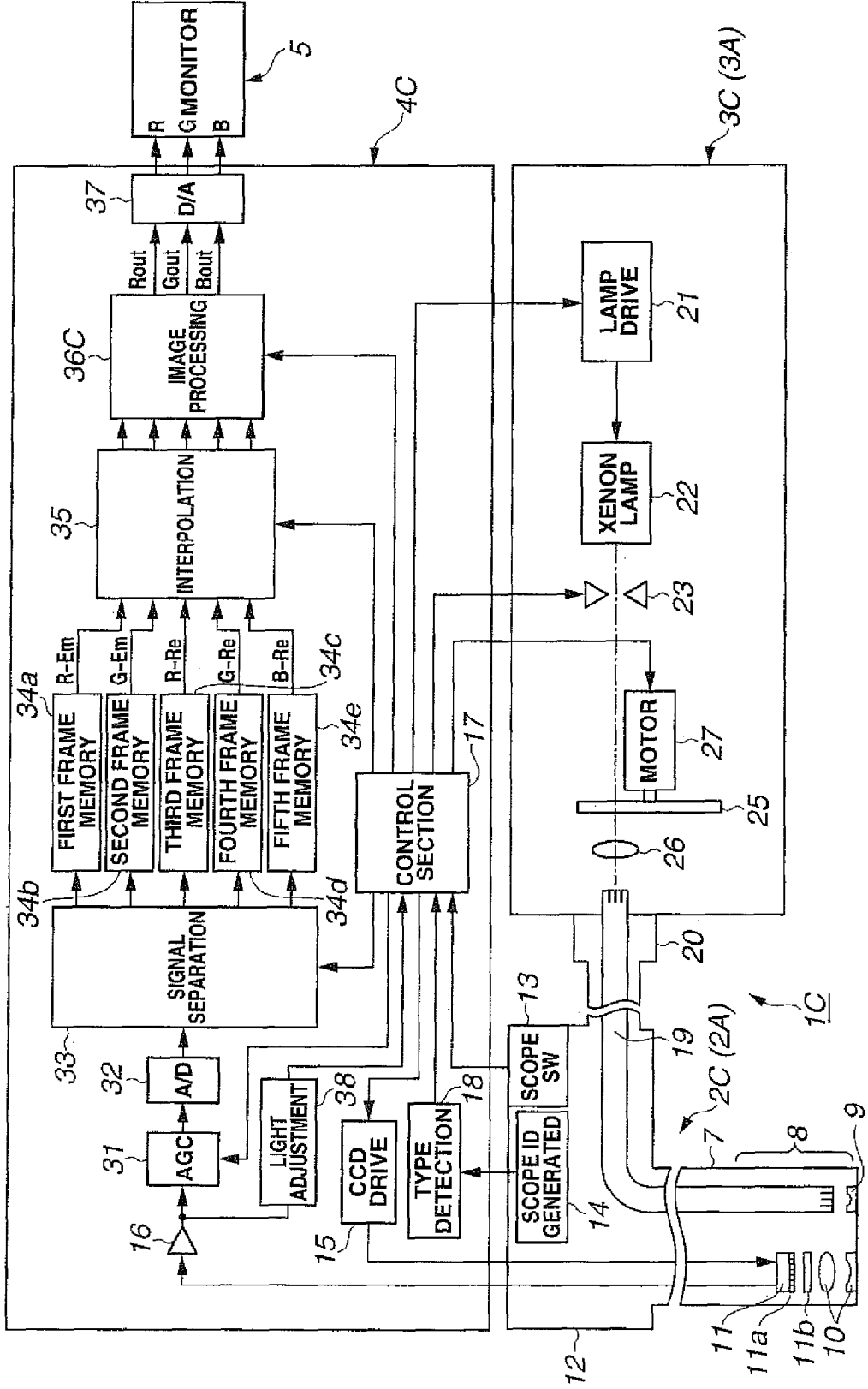
FIG. 12 is a block diagram illustrating an overall configuration of a fluorescent imaging device according to a modification example of the second embodiment.

FIG. 12 illustrates a configuration of a fluorescent imaging device 1C according to a modification example of the second embodiment. The fluorescent imaging device 1C is constructed of an endoscope 2C, a light source section 3C, a processor 4C and a monitor 5. The endoscope 2C according to the present modification example has the same configuration as that of the simultaneous type endoscope 2A according to the first embodiment and the light source section 3C also has the same configuration as that of the light source section 3A of the first embodiment.

Furthermore, the processor 4C of the present modification example adopts an image processing circuit 36C that performs image processing different from that of the image processing circuit 36 in the processor 4A of the first embodiment.

Figure 13:
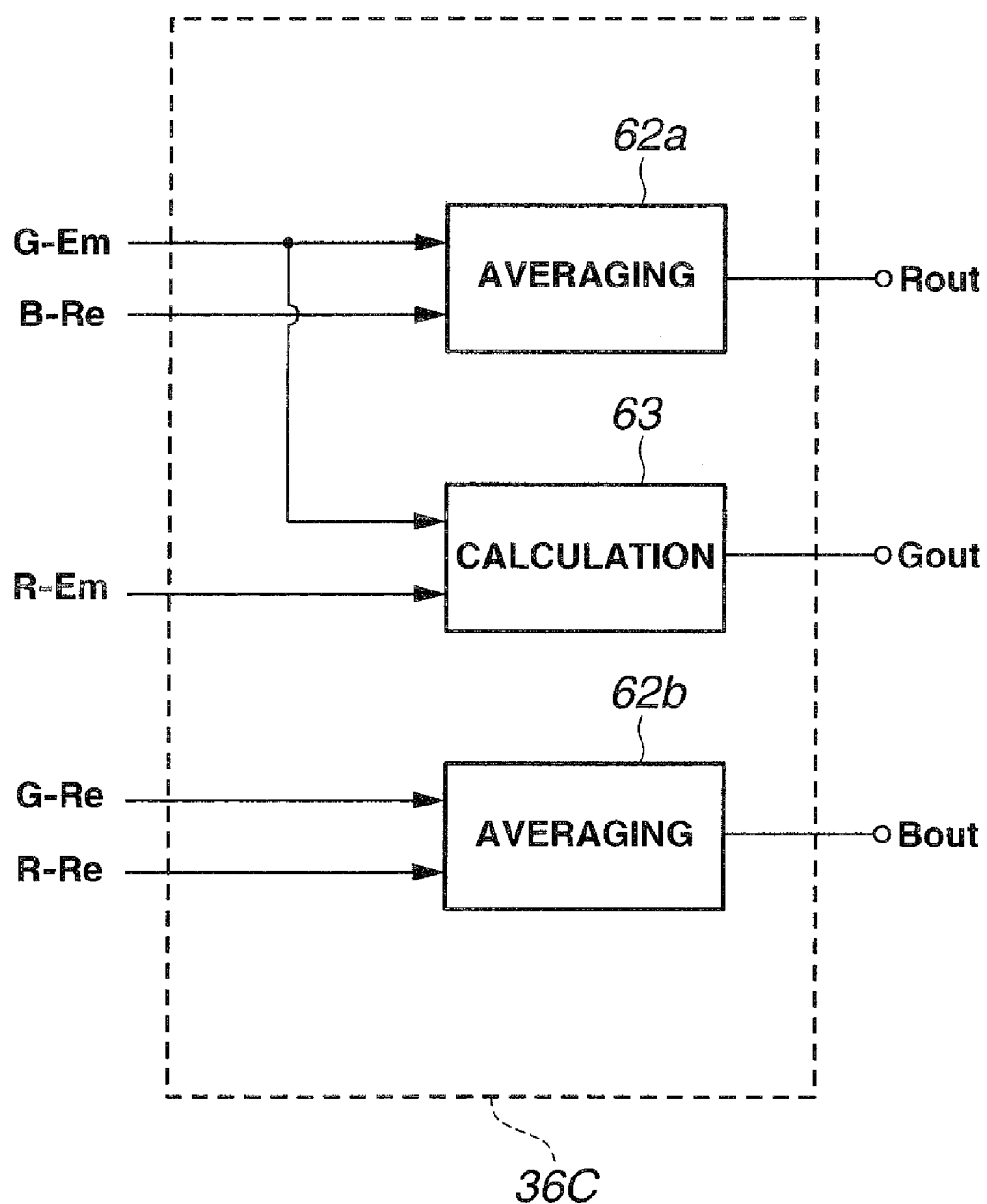
FIG. 13 is a block diagram illustrating a configuration of the image processing circuit according to the modification example of the second embodiment.

FIG. 13 illustrates a configuration of the image processing circuit 36C according to the present modification example.

An image signal G-Em of a fluorescent image G-Em (i, j) and an image signal B-Re of a reflected light image B-Re (i, j) are inputted to an averaging circuit 62a, subjected to averaging processing and outputted as an image signal Rout. That is, $$Rout(i,j) = \{G\text{-}Em(i,j) + B\text{-}Re(i,j)\}/2 \qquad (8)$$

The image signal G-Em of the fluorescent image G-Em (i, j) and the image signal R-Em of the fluorescent image R-Em (i, j) are inputted to a calculation circuit 63, subjected to the same calculation processing as that of the second calculation circuit 47 according to the first embodiment and outputted as an image signal Gout.

That is, $$Gout(i,j) = \{G\text{-}Em(i,j) + R\text{-}Em(i,j) + 32 \log(G\text{-}Em(i,j)/(R\text{-}Em(i,j)))\}/3 \qquad (9)$$

Furthermore, both image signals G-Re and R-Re of the reflected light images G-Re (i, j) and R-Re (i, j) are inputted to an averaging circuit 62b, subjected to averaging processing and outputted as an image signal Bout.

$$Bout(i,j) = \{G\text{-}Re(i,j) + R\text{-}Re(i,j)\}/2 \qquad (10)$$

The image processing circuit 36C then outputs image signals of the images in Expressions 8 to 10 to the R, G and B channels of the monitor 5 via the D/A conversion circuit 37 and the monitor 5 displays the images in Expressions 8 to 10 in color as diagnostic fluorescent images.

The present modification example has the following effects.

Even when the fluorescence is separated into different components to pick up an image, it is possible to suppress the contrast of the normal mucous membrane accompanied by mucous membrane hypertrophy through averaging processing between the fluorescent image and the reflected light image of the blue reference light and reduce more noise than when only the fluorescent image is outputted.

Furthermore, noise can be reduced by also averaging reflected light images of red and green reference light.

As will be described later in FIG. 25, the present embodiment may also have a configuration provided with a function of sequentially irradiating wideband R, G and B illuminating light beams, performing frame sequential color image pickup and displaying normal color images on the monitor 5.

Third Embodiment

Next, a third embodiment of the present invention will be described with reference to FIG. 14 to FIG. 16. Conventionally, one wideband excitation light beam is irradiated to thereby excite fluorescence, and it is thus impossible to detect fluorescence radiation from different substances or a difference in fluorescence radiation from one mucosal layer to another, and thus the conventional method is not suited to the detection of a variety of lesions.

Furthermore, since auto fluorescence is influenced by absorption by blood, it is difficult to discriminate between an inflammation and a tumor based on image information with only auto fluorescence images. Thus, the present embodiment makes it easier to identify between a tumor and an inflammation by adopting the following configuration. FIG. 14 illustrates a configuration of a fluorescent imaging device 1D according to a third embodiment of the present invention.

The fluorescent imaging device 1D is constructed of an endoscope 2D, a light source section 3D, a processor 4D and a monitor 5.

The endoscope 2D is an endoscope provided with a monochrome CCD 11 and has the same configuration as that of the endoscope 2B in FIG. 8. However, the excitation light cut filter (denoted by reference numeral 11d) has filter characteristics that cut excitation light of two wavelength bands which will be described below (see FIG. 16).

Furthermore, the rotation filter 25 of the light source section 3D is provided with three filters as in the case of FIG. 9. However, the present embodiment has two excitation light filters 6Ex1 and 6Ex2 that generate excitation light of different wavelengths as shown in FIG. 15 and a filter 6Re (G) that irradiates one reference light beam, for example, light of a green wavelength band.

Figure 16:
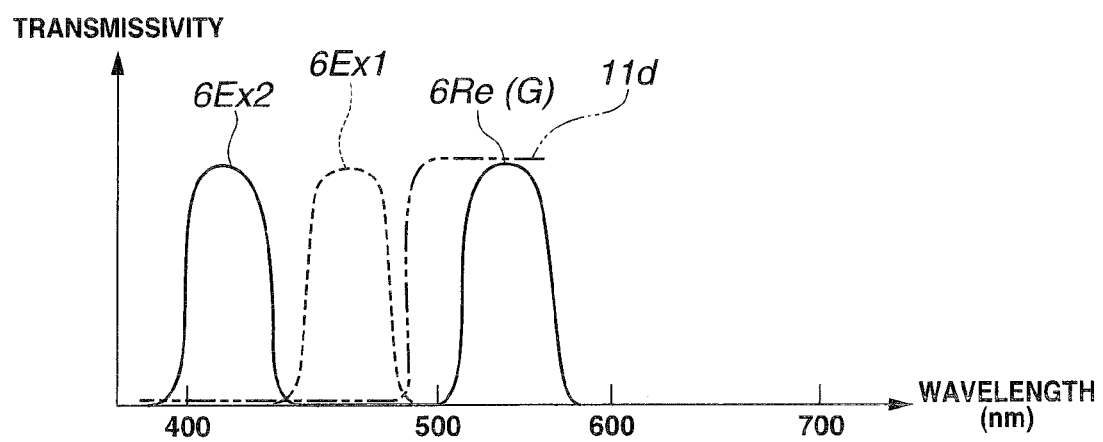
FIG. 16 is a diagram illustrating transmission characteristics of the excitation light filter or the like provided in the rotation filter in FIG. 15.

FIG. 16 illustrates three filter transmission characteristics. The two excitation light filters 6Ex1 and 6Ex2 are set to characteristics that allow to pass a longer wavelength band of blue light and a shorter wavelength band of blue light respectively. The light source section 3D then generates two excitation light beams and a green wavelength light beam and sequentially emits those light beams to the endoscope 2D.

The CCD 11 picks up a fluorescence image generated from a biological mucous membrane or the like as the object to be examined with the two excitation light filters 6Ex1 and 6Ex2 and also picks up a reflected light image in the case of reference light, and outputs the three image pickup signals to the processor 4D.

To be more specific, the CCD 11 outputs an image pickup signal of fluorescence by first excitation light through the excitation light filter 6Ex1 and an image pickup signal of fluorescence by second excitation light through the excitation light filter 6Ex2 to the processor 4D.

A multiplexer 33B of the processor 4D performs switching using the image pickup signal of fluorescence by the first excitation light and the image pickup signal of fluorescence by the second excitation light so as to select the first frame memory 34a and the second frame memory 34b and stores the image pickup signals in a first frame memory 34a and a second frame memory 34b as image signals Em1 and Em2 respectively. Furthermore, the multiplexer 33B stores the image pickup signal of reflected light of the reference light in a third frame memory 34c as an image signal G-Re.

Furthermore, the processor 4D adopts the configuration of the processor 4B in FIG. 8 in which the image signals Em1, Em2 and G-Re read from the first frame memory 34a to the third frame memory 34c are outputted to the D/A conversion circuit 37 as they are.

In this case, the image signals Em1, Em2 and G-Re are outputted to the R, G, and B channels of the monitor 5 respectively and displayed in color on the monitor 5 as endoscope fluorescent images.

Figure 14:
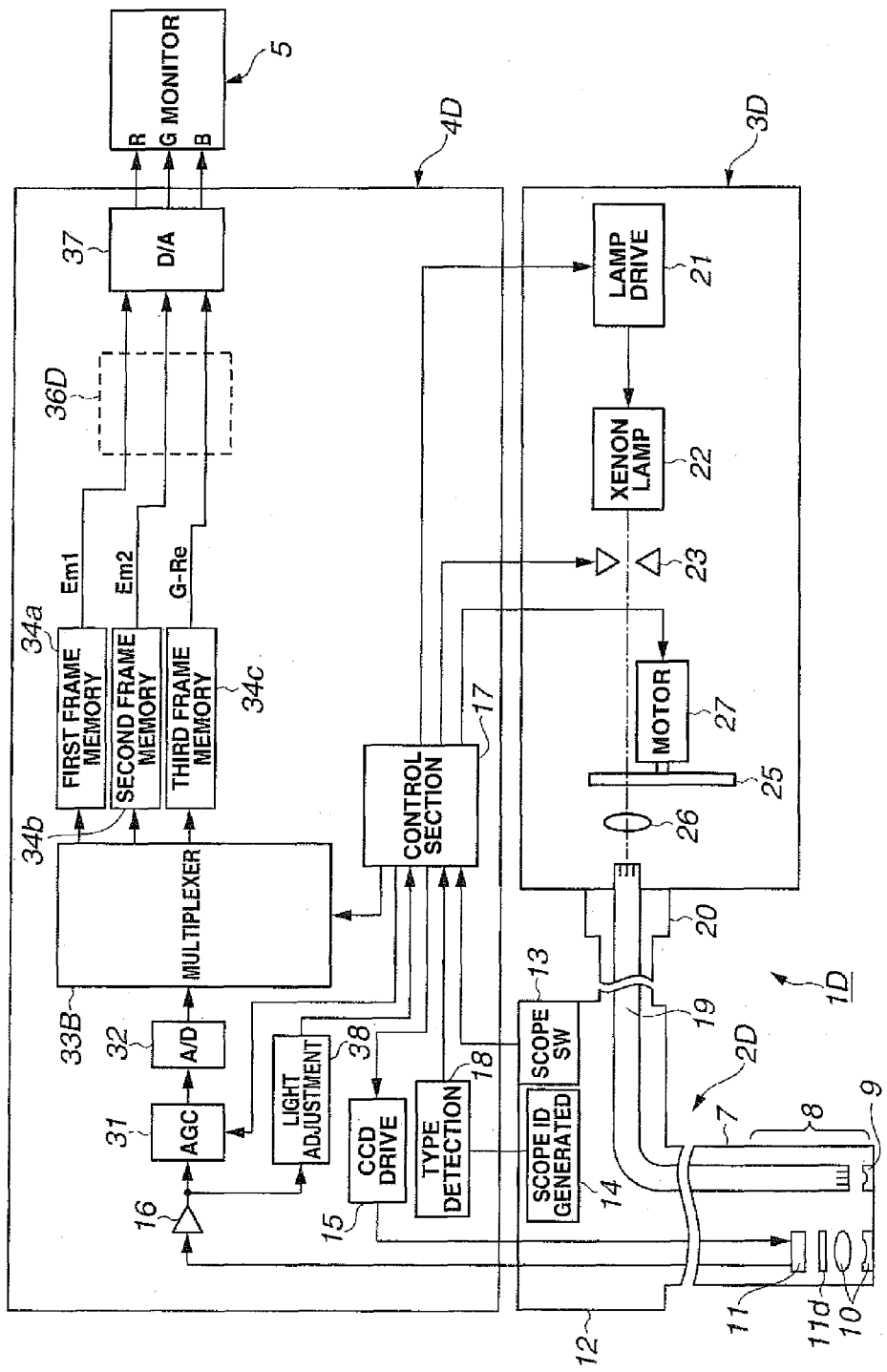
FIG. 14 is a block diagram illustrating an overall configuration of a fluorescent imaging device according to a third embodiment of the present invention.
Figure 15:
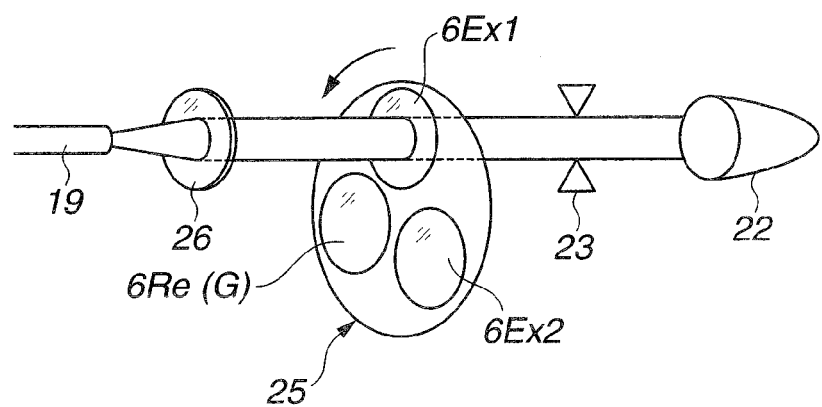
FIG. 15 is a diagram illustrating a configuration of a peripheral part of the rotation filter in the light source section.

An image processing circuit 36D shown by a dotted line in FIG. 14 is an image processing circuit in the modification example of the present embodiment.

The rest of the configuration is the same as that of the second embodiment.

The present embodiment has the following effects in a simple configuration.

Using two excitation light beams Ex1 and Ex2 of a long wavelength band and a short wavelength band in the blue color wavelength band allows fluorescent substances distributed in different mucosal layers to be excited and detected and allows fluorescent substances which differ from each other due to differences in wavelength of excitation light to be detected, and thereby improves the function of selective detection.

In other words, using different fluorescent substances depending on the lesion allows various types of lesion to be detected. Moreover, adding an image signal of the reflected light image of a green reflected light image allows a tumor to be extracted in a color tone different from that of an inflammation.

Furthermore, since the wavelength demonstrates different transmission characteristics in a depth direction, it is possible to make a selective fluorescence observation in different depths depending on the depth direction of the mucous membrane.

As a modification example of the present embodiment, for example, the image processing circuit 36D shown by the dotted line in FIG. 14 may be provided. The image processing circuit 36D may perform the following calculation.

To be more specific, a calculation:

$$Rout(i,j) = Gout(i,j) = 32 \log(Em1(i,j)/Em2(i,j)) + Em2(i,j) \quad (11)$$

is performed on the fluorescent images $Em1(i, j)$ and $Em2(i, j)$ and image signals of the calculated images are outputted to the R channel and G channel of the monitor 5.

Furthermore, the reflected light image G-Re (B) (i, j) is outputted to the B channel of the monitor 5. That is, $$Bout(i,j) = G\text{-}Re(B)(i,j) \quad (12)$$

The present modification example also has substantially the same effects as those of the third embodiment. In addition, red reference light may be added and light of four bands may be used. In such a case, calculation processing may be performed by changing above described Expression 11 using an image signal R-Re of reflected light by red reference light. To be more specific, $$Rout(i,j) = R\text{-}Re(i,j)$$

Expression 11 is used for the image signal Gout.

Fourth Embodiment

Figure 17:
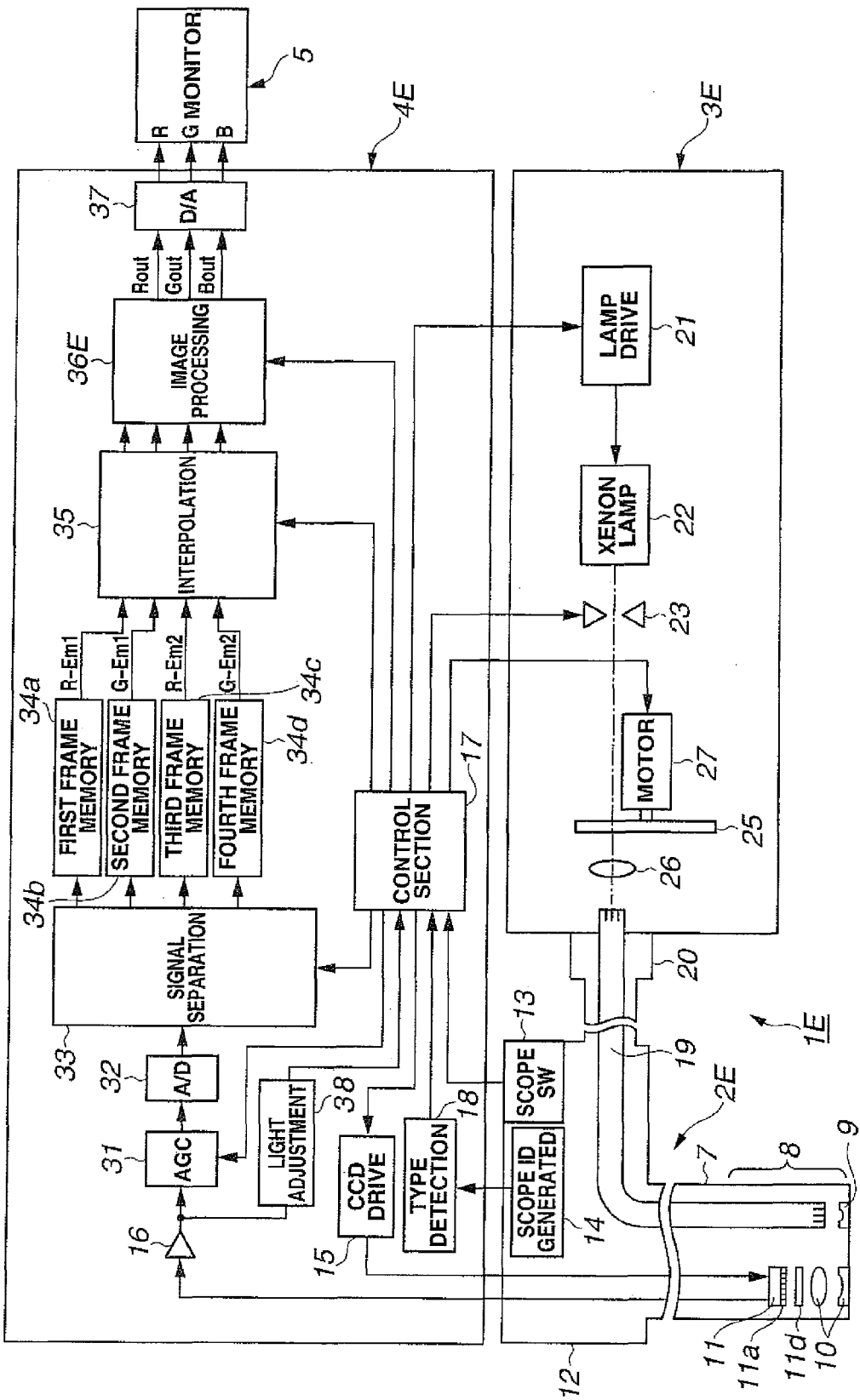
FIG. 17 is a block diagram illustrating an overall configuration of a fluorescent imaging device according to a fourth embodiment of the present invention.

Next, a fourth embodiment of the present invention will be described with reference to FIG. 17 and FIG. 18. The present embodiment is intended to provide a fluorescent imaging device suited to detection of a variety of lesions such as detection of fluorescence radiation from different substances or difference in fluorescence radiation from one mucosal layer to another. FIG. 17 illustrates a configuration of a fluorescent imaging device 1E according to a fourth embodiment of the present invention.

This fluorescent imaging device 1E is constructed of an endoscope 2E, a light source section 3E, a processor 4E and a monitor 5.

The endoscope 2E of the present embodiment adopts a simultaneous type endoscope provided with a color filter 11a in the same way as in the first embodiment. However, the excitation light cut filter 11d of the present embodiment is the same as that of the third embodiment. The excitation light cut filter 11d has a characteristic that allows to pass a longer wavelength side than the green wavelength band as shown in FIG. 16.

Figure 18:
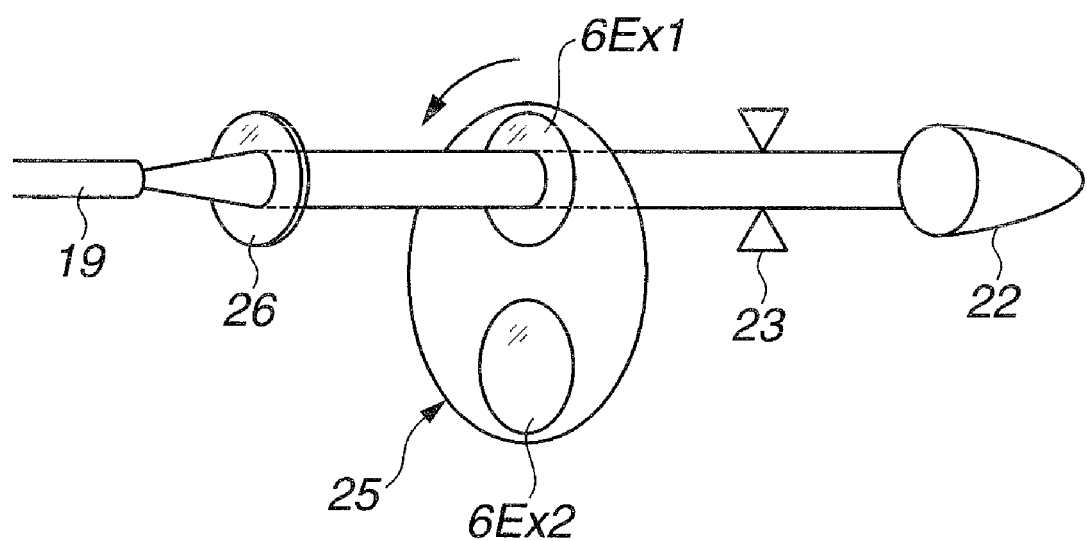
FIG. 18 is a diagram illustrating a configuration of a peripheral part of the rotation filter in the light source section.

Furthermore, as shown in FIG. 18, the light source section 3E is provided with the two excitation light filters 6Ex1 and 6Ex2 described in the third embodiment attached to the rotation filter 25. Therefore, the light source section 3E emits first excitation light and second excitation light.

The color filter 11a optically separates red and green fluorescence images radiated from the biological mucous membrane side when the first excitation light and the second excitation light are irradiated from the two excitation light filters 6Ex1 and 6Ex2 on the image pickup surface of the CCD 11 making up the simultaneous type image pickup means provided with the excitation light cut filter 11d. The respective image pickup signals of fluorescence picked up are outputted to the processor 4E.

The processor 4E has four frame memories 34a to 34d instead of the five frame memories 34a to 34e in the processor 4A in FIG. 1. Furthermore, in this case, the signal separation circuit 33 performs switching at timing at which signal components of R and G pixels are inputted during a period over which the image pickup signal of first fluorescence is inputted and stores the image pickup signals in the first frame memory 34a and the second frame memory 34b as image signals of fluorescence R-Em1 and G-Em1.

Likewise, for a period over which the image pickup signal of the second fluorescence is inputted, the signal separation circuit 33 performs switching at timing at which signal components of R and G pixels are inputted and stores the fluorescence image signals R-Em2 and G-Em2 in the third frame memory 34c and the fourth frame memory 34d.

The four fluorescence image signals R-Em1, G-Em1, R-Em2 and G-Em2 read from the frame memories 34a to 34d are subjected to pixel interpolation processing by the interpolation circuit 35 and then subjected to image processing by the image processing circuit 36E as follows.

$$Rout(i,j) = 32 \log(R\text{-}Em1(i,j)/G\text{-}Em1(i,j)) \quad (13)$$

$$Gout(i,j) = G\text{-}Em1(i,j) \quad (14)$$

$$Bout(i,j) = 32 \log(R\text{-}Em2(i,j)/G\text{-}Em2(i,j)) \quad (15)$$

These images Rout(i, j), Gout(i, j) and Bout(i, j) are outputted to the R, G and B channels of the monitor 5 respectively and displayed in color on the monitor 5.

The present embodiment has the following effects.

Using two excitation light beams of a long wavelength band and a short wavelength band in a blue color wavelength band allows fluorescent substances distributed in different mucosal layers to be excited and detected and allows different fluorescent substances to be detected due to differences in excitation wavelength and thereby improves the detection function for a variety of lesions.

Fifth Embodiment

Next, a fifth embodiment of the present invention will be described with reference to FIG. 19 to FIG. 21. The present embodiment is intended to provide a fluorescent imaging device suited to detection of a variety of lesions such as enabling fluorescence observations to be made of mucosal layers having different depths.

Figure 19:
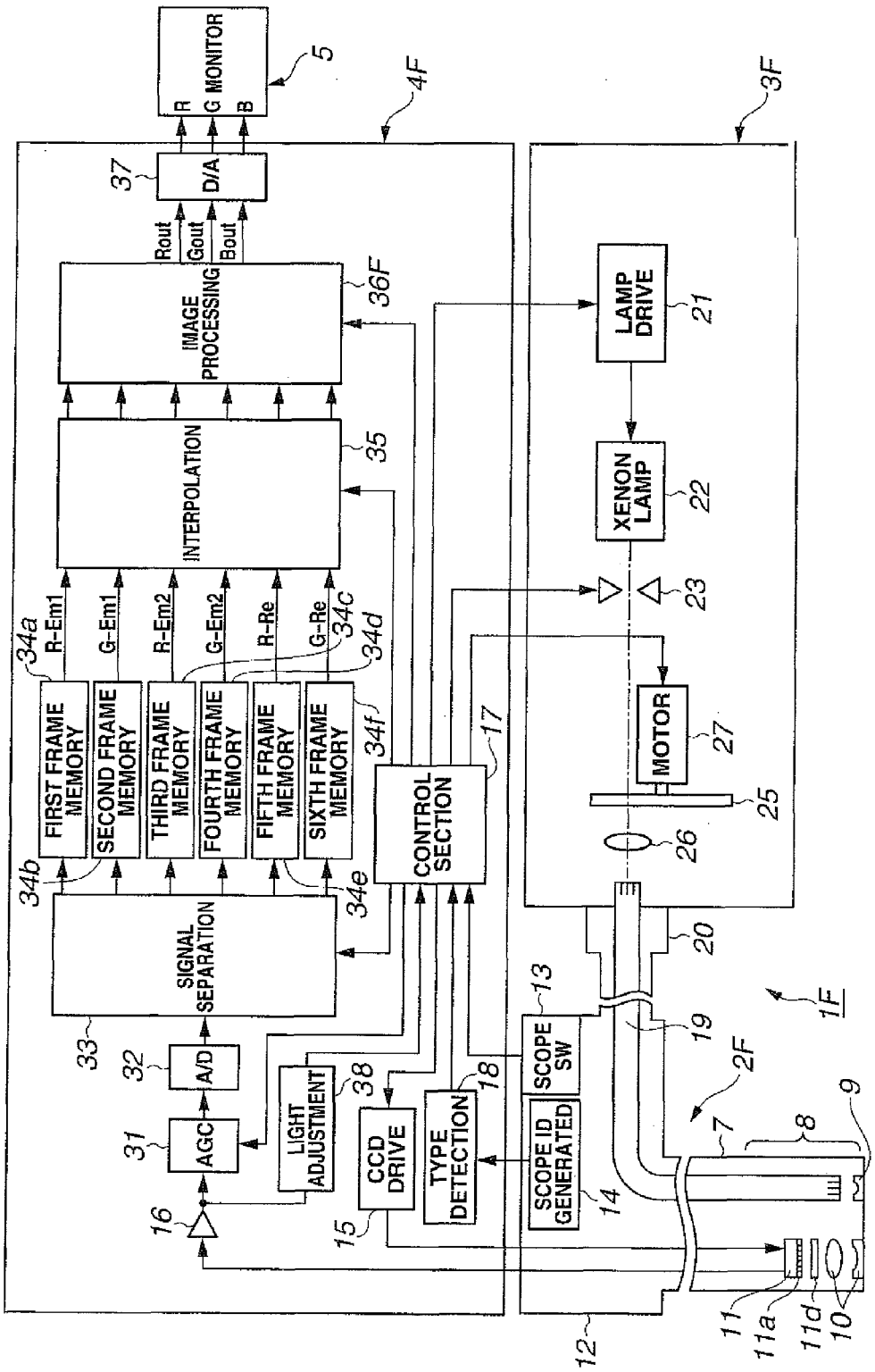
FIG. 19 is a block diagram illustrating an overall configuration of a fluorescent imaging device according to a fifth embodiment of the present invention.

FIG. 19 illustrates a configuration of a fluorescent imaging device 1F according to a fifth embodiment of the present invention.

The fluorescent imaging device 1F is constructed of an endoscope 2F, a light source section 3F, a processor 4F and a monitor 5.

The endoscope 2F of the present embodiment is the same as the endoscope 2E of the fourth embodiment. That is, the endoscope 2F is a simultaneous type endoscope provided with a color filter 11a and is also provided with an excitation light cut filter 11d.

Figure 20:
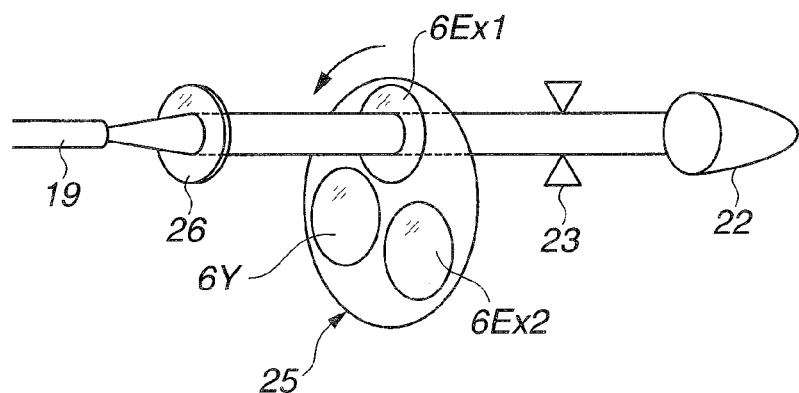
FIG. 20 is a diagram illustrating a configuration of a peripheral part of the rotation filter in the light source section.

Furthermore, as shown in FIG. 20, the light source section 3F is provided with, for example, a Y filter 6Y attached to the rotation filter 25 for irradiating reference light in addition to the two excitation light filters 6Ex1 and 6Ex2 described in the fourth embodiment shown in FIG. 18. That is, the rotation filter 25 is provided with the three filters 6Ex1, 6Ex2 and 6Y.

Figure 21:
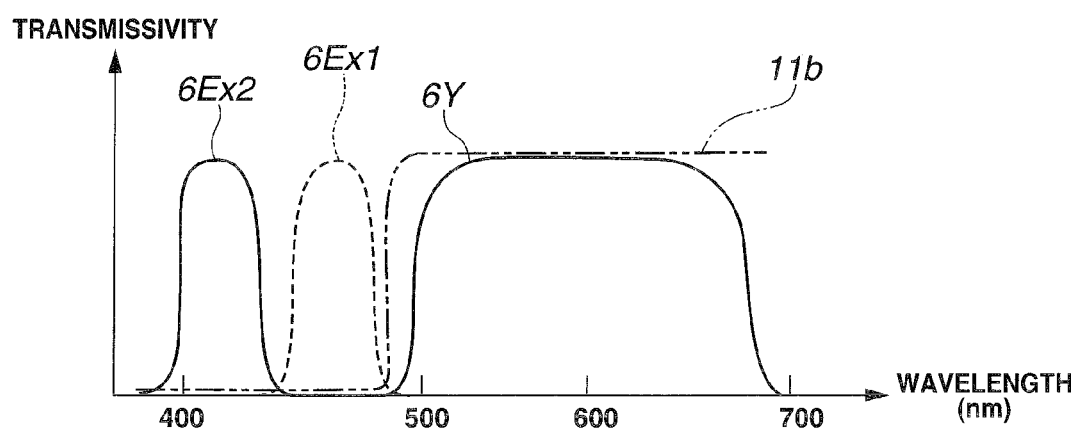
FIG. 21 is a diagram illustrating transmission characteristics of the excitation light filter or the like provided in the rotation filter in FIG. 20.

FIG. 21 illustrates transmission characteristics of the three filters 6Ex1, 6Ex2 and 6Y.

The light source section 3E then sequentially emits first excitation light and second excitation light of a blue wavelength band and reference light of green to red wavelength bands through the Y filter 6Y.

The present embodiment corresponds to the configuration of the fourth embodiment further irradiating reference light of Y and picking up a reflected light image from a biological mucous membrane. The color filter 11a also extracts R and G components for the reflected light image.

Therefore, the processor 4F according to the present embodiment is provided with a fifth frame memory 34e and a sixth frame memory 34f as two frame memories for storing R and G image signals R-Re and G-Re of the reflected light image in addition to the four frame memories 34a to 34d of the fourth embodiment.

Furthermore, the signal separation circuit 33 performs the operation for a period of picking up a fluorescence image in the same way as in the fourth embodiment and for a period of picking up a reflected light image by the reference light, the signal separation circuit 33 stores the image signals R-Re and G-Re in the fifth frame memory 34e and the sixth frame memory 34f respectively.

Furthermore, the image processing circuit 36F of the processor 4F of the present embodiment performs the following calculations.

$$Rout(i,j)=32 \log(R\text{-}Em1(i,j)/G\text{-}Em1(i,j)) \quad (16)$$

$$Gout(i,j)=32 \log(R\text{-}Em2(i,j)/G\text{-}Em2(i,j)) \quad (17)$$

$$Bout(i,j)=32 \log(G\text{-}Re(i,j)/R\text{-}Re(i,j)) \quad (18)$$

The present embodiment has the following effects.

Using two excitation light beams of a long wavelength band and a short wavelength band in the blue color wavelength band allows fluorescent substances distributed in different mucosal layers to be excited and detected and also allows fluorescent substances which differ from each other due to differences in wavelength of excitation light to be detected, and can thereby detect a variety of lesions. Furthermore, it is possible to generate fluorescent images suited to detection of a variety of lesions.

Furthermore, since fluorescence can be spectroscopically detected, it is possible to generate a high contrast image which makes it possible to easily identify between a region of normal tissue and a region of tumorous tissue.

Furthermore, since the simultaneous type CCD 11 provided with the color filter 11a is used to pickup images, it is possible to optically separate and detect fluorescence, thereby improve the contrast by hemoglobin (Hb) absorption of vascular hyperplasia or the like by auto fluorescence of a green band and detect a variation in color tone of auto fluorescence in the normal tissue and tumorous tissue.

Furthermore, it is possible to extract tumorous tissue in a color tone different from that of inflammation tissue by adding (generating) an image of green reflected light, extract fluorescence attenuation in the tumorous tissue and an intensity reduction of fluorescence due to an illumination distance distinctively from each other by adding (generating) an image of red reflected light, and therefore the mechanism of detection and diagnosis also improves. Furthermore, the image by red and green reflected light also has a merit of being able to be generated by the CCD 11 provided with the color filter 11a by one illumination and by one image pickup operation.

As a modification example of the present embodiment, the image processing circuit 36F may also perform the following calculations.

$$Rout(i,j)=32 \log(R\text{-}Em1(i,j)/G\text{-}Em1(i,j))+R\text{-}Re(i,j) \quad (19)$$

$$Gout(i,j)=32 \log(R\text{-}Em2(i,j)/G\text{-}Em2(i,j))+R\text{-}Re(i,j) \quad (20)$$

$$Bout(i,j)=32 \log(G\text{-}Re(i,j)/R\text{-}Re(i,j))+R\text{-}Re(i,j) \quad (21)$$

The present modification example has substantially the same effects as those of the fifth embodiment.

Sixth Embodiment

Next, a sixth embodiment of the present invention will be described with reference to FIG. 22. The present embodiment is intended to provide a fluorescent imaging device that facilitates detection of a variation in color tone of auto fluorescence in normal tissue and a tumor.

Figure 22:
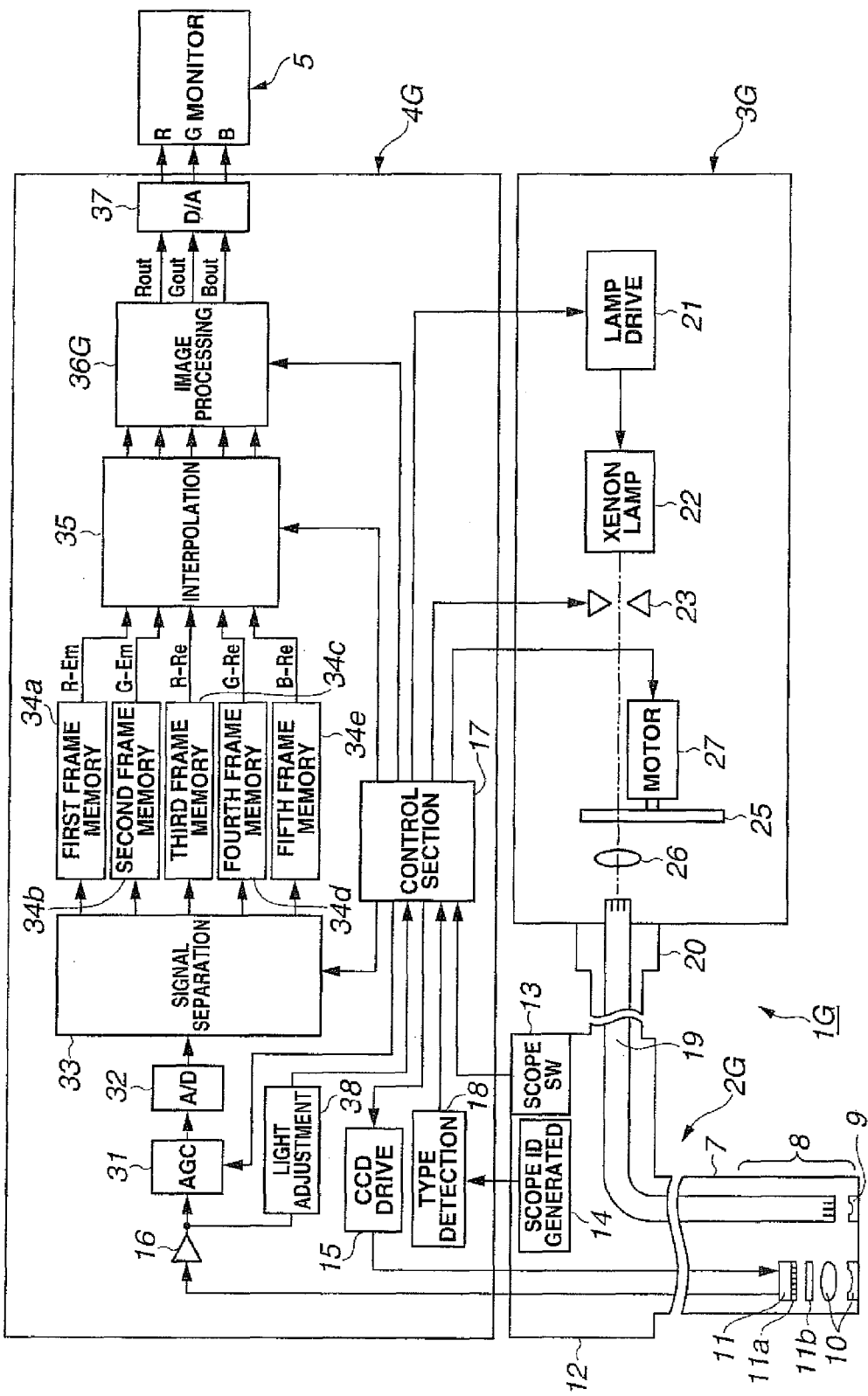
FIG. 22 is a block diagram illustrating an overall configuration of a fluorescent imaging device according to a sixth embodiment of the present invention.

FIG. 22 illustrates a configuration of a fluorescent imaging device 1G according to a sixth embodiment of the present invention. The fluorescent imaging device 1G is constructed of an endoscope 2G, a light source section 3G, a processor 4G and a monitor 5. The endoscope 2G of the present embodiment is the same endoscope as the endoscope 2A of the first embodiment. That is, the endoscope 2G is a simultaneous type endoscope provided with a color filter 11a and is also provided with an excitation light cut filter 11b.

Furthermore, the light source section 3G also has the same configuration as that of the light source section 3A of the first embodiment. That is, the rotation filter 25 as shown in FIG. 2 is provided with the excitation light filter 6Ex and the reference light filter 6Re.

The CCD 11 outputs two types of image pickup signals in the same way as in the first embodiment, that is, an image pickup signal of fluorescence and an image pickup signal of reflected light, to the processor 4G. As in the case of the first embodiment, five image signals R-Em, G-Em, R-Re, G-Re and B-Re are stored in a first frame memory 34a to the fifth frame memory 34e respectively.

The processor 4G corresponds to the processor 4A of the first embodiment provided with an image processing circuit 36G that performs image processing different from that of the image processing circuit 36 and the rest of the configuration is the same as that of the first embodiment.

To be more specific, the image processing circuit 36G performs the following calculations.

$$Rout(i,j)=32 \log(R\text{-}Em(i,j)/G\text{-}Em(i,j)) \quad (22)$$

$$Gout(i,j)=G\text{-}Re(i,j) \quad (23)$$

$$Bout(i,j)=32 \log(G\text{-}Re(i,j)/R\text{-}Re(i,j)) \quad (24)$$

The present embodiment has the following effects.

Since the CCD 11 provided with the color filter 11a can separate fluorescence into different components and pick up images thereof, and can thereby capture a spectral variation of auto fluorescence in normal tissue and tumorous tissue and provide images which make it possible to easily identify between both types of tissue.

Furthermore, since green fluorescence which is easily absorbed by hemoglobin can be selectively detected, sensitivity improvement can be expected.

Furthermore, using blue reflected light of shorter wavelength than excitation light allows a fine structure of a mucosal epithelium that cannot be obtained by auto fluorescence to be extracted, makes it easier to identify or differentiate between inflammation tissue and tumorous tissue, and can thereby reduce the occurrence of pseudopositive reaction.

As a modification example of the present embodiment, the image processing circuit 36G may perform the following calculations.

$$Rout(i,j)=32 \log(R\text{-}Em(i,j)/G\text{-}Em(i,j))+R\text{-}Re(i,j) \qquad (25)$$

$$Gout(i,j)=G\text{-}Re(i,j) \qquad (26)$$

$$Bout(i,j)=32 \log(G\text{-}Re(i,j)/R\text{-}Re(i,j))+R\text{-}Re(i,j) \qquad (27)$$

The present modification example has substantially the same effects as those of the sixth embodiment.

Seventh Embodiment

Next, a seventh embodiment of the present invention will be described with reference to FIG. 23. The present embodiment is intended to provide a fluorescent imaging device capable of extracting a fine blood vessel structure of a mucosal epithelium.

Figure 23:
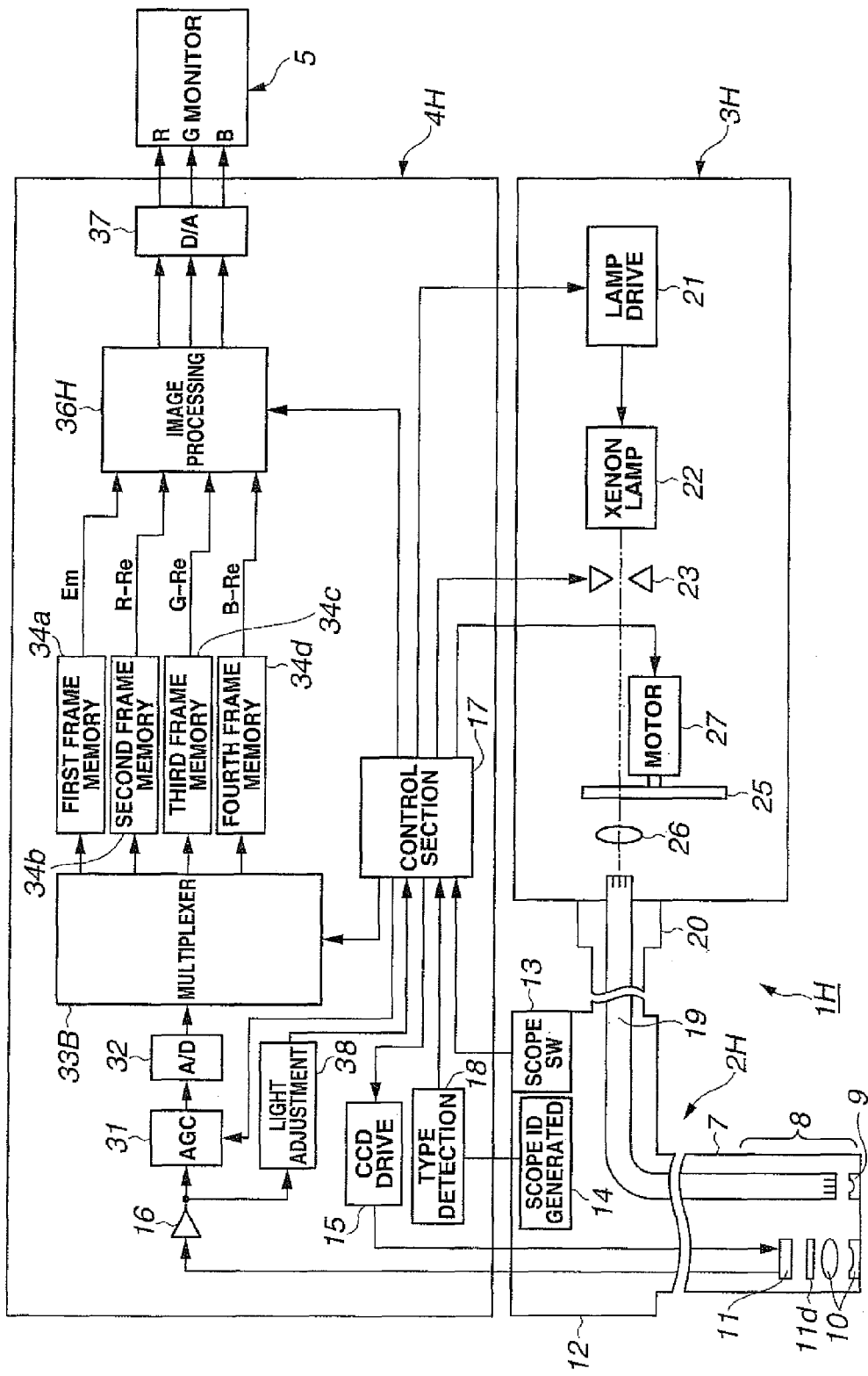
FIG. 23 is a block diagram illustrating an overall configuration of a fluorescent imaging device according to a seventh embodiment of the present invention.

FIG. 23 illustrates a configuration of a fluorescent imaging device 1H according to the seventh embodiment of the present invention. The fluorescent imaging device 1H is constructed of an endoscope 2H, a light source section 3H, a processor 4H and a monitor 5. The endoscope 2H of the present embodiment is the same as the endoscope 2B of the second embodiment shown in FIG. 8.

That is the endoscope 2H is a frame sequential type endoscope that adopts a monochrome CCD 11 and is provided with an excitation light cut filter 11b.

Figure 24:
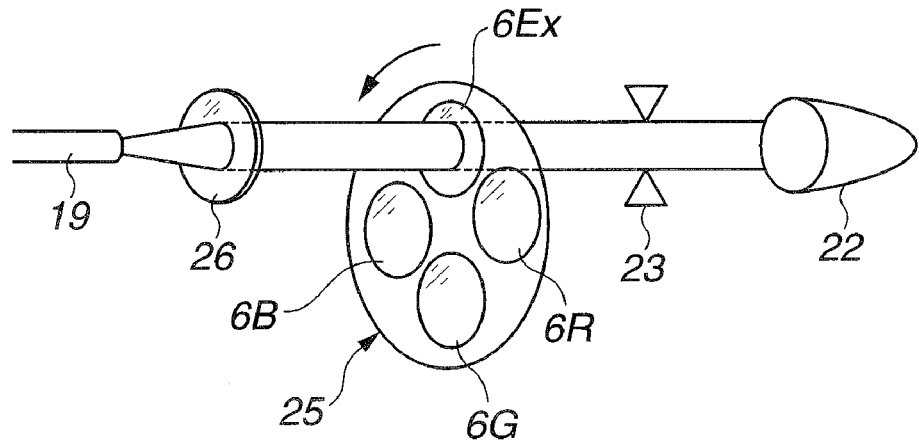
FIG. 24 is a diagram illustrating a configuration to a peripheral part of the rotation filter in the light source section.

Furthermore, the light source section 3H corresponds to the light source section 3B of the second embodiment having a configuration with the rotation filter 25 provided with four filters instead of three filters. That is, as shown in FIG. 24, the rotation filter 25 is provided with an excitation light filter 6Ex and reference light filters 6R, 6G and 6B that allow to pass R, G and B of narrow bands.

In this case, the excitation light filter 6Ex and the reference light filter 6B are the same as those used in the second embodiment.

Furthermore, the filters 6R and 6G are set to characteristics that allow to pass the red and green narrow bands respectively (e.g., the same as those of 6R and 6G in FIG. 3).

The light source section 3H then sequentially emits excitation light and reference light of three wavelength bands. Furthermore, the CCD 11 picks up a fluorescence image of excitation light and reflected light images of three reference light beams and outputs the images to the processor 4H.

The processor 4H corresponds to the processor 4B in FIG. 8 provided with four frame memories 34a to 34d, that is, one frame memory 34d added to the three frame memories 34a to 34c.

The control section 17 performs switching control of the multiplexer 33B and stores an image signal Em of fluorescence which is a picked up fluorescence image in the first frame memory 34a and stores image signals R-Re, G-Re and B-Re of reflected light of R, G and B in the second frame memory 34b to the fourth frame memory 34d respectively.

Furthermore, instead of the image processing circuit 36B in FIG. 8, the present embodiment uses an image processing circuit 3614 that performs different image processing.

The image processing circuit 36H performs the following calculations.

$$Rout(i,j)=32 \log(Em(i,j)/B\text{-}Re(i,j)) \qquad (28)$$

$$Gout(i,j)=Em(i,j) \qquad (29)$$

$$Bout(i,j)=32 \log(G\text{-}Re(i,j)/R\text{-}Re(i,j)) \qquad (30)$$

The present embodiment has the following effects.

Using the blue reflected light allows hemoglobin absorption to be detected with high contrast and allows a fine blood vessel structure of a mucosal epithelium to be extracted.

Furthermore, a combination with a fluorescent image allows states of hemoglobin and mucous membrane hypertrophy to be extracted in different color tones, makes it easier to discriminate between an inflammation and a tumorous lesion, can reduce the occurrence of pseudopositive reaction and improves the function of a screening diagnosis.

Figure 25:
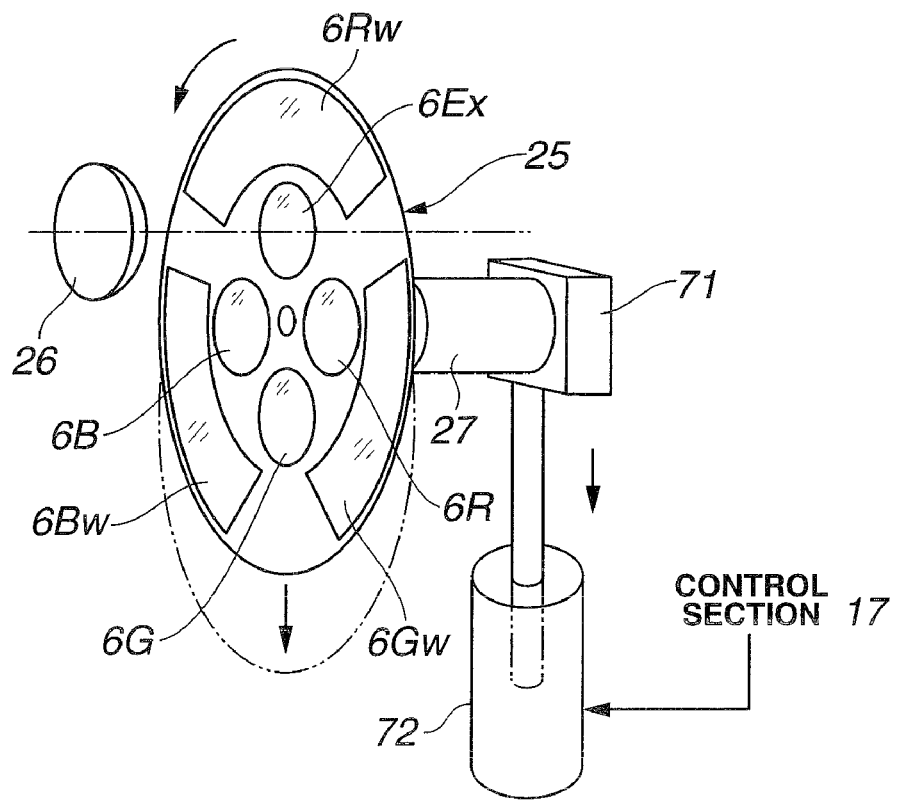
FIG. 25 is a diagram illustrating a configuration of a peripheral part of the rotation filter according to a modification example.

The rotation filter 25 having a configuration according to a modification example shown in FIG. 25 may be adopted for the light source section 3H of the present embodiment in FIG. 23.

The present modification example provides the above described four filters 6Ex, 6R, 6G and 6B on the inner circumferential side of the rotation filter 25 as shown in FIG. 25 and provides R, G and B filters 6Rw, 6Gw and 6Bw that allow to pass R, G and B light beams of normal widebands on the outer circumferential side.

Furthermore, for example, an electromagnetic plunger 72 is provided as a moving mechanism that moves a holding member 71 that holds a motor 27 for rotating the rotation filter 25 in a direction perpendicular to the optical path. The operation of the electromagnetic plunger 72 is controlled by the control section 17.

When used as the fluorescent imaging device 1H of the aforementioned seventh embodiment, that is, used in a fluorescence observation mode, the control section 17 sets the four filters 6Ex, 6R, 6G and 6B on the inner circumferential side so as to be sequentially inserted in the optical path as shown in FIG. 25. The fluorescence observation mode corresponds to the aforementioned operation.

When selecting a normal observation mode for making a normal observation, the operator operates an observation mode selection switch provided in, for example, the scope switch 13. An operation signal of the observation mode selection switch is inputted to the control section 17, and upon recognizing that it is an instruction for a normal observation mode, the control section 17 supplies a drive current to an electromagnet of the electromagnetic plunger 72 and moves a movable rod by suction downward in FIG. 25.

This movement causes the rotation filter 25 to move downward (direction perpendicular to the optical path) as shown by a two-dot dashed line. In this state, the three R, G and B filters 6Rw, 6Gw and 6Bw on the outer circumferential side are sequentially inserted in the optical path.

The R, G and B filters 6Rw, 6Gw and 6Bw cause the object to be examined to be irradiated with frame sequential R, G and B light beams. The reflected light image irradiated with frame sequential R, G and B light beams and reflected by the object to be examined is picked up by the CCD 11 and the image pickup signals of R, G and B are inputted to the processor 4H.

The control section 17 controls switching of the multiplexer 33B and stores image signals R-Re, G-Re and B-Re of the reflected light image in the first frame memory 34a to the third frame memory 34c.

The R, G and B image signals stored in the first frame memory 34a to the third frame memory 34c pass through the image processing circuit 36H and the D/A conversion circuit 37 and are outputted to the R, G and B channels of the monitor 5. A normal image is displayed in color on the monitor 5. The present invention may adopt the configuration provided with a function of making a normal observation in this way. Moreover, such a configuration may be applied to the other embodiments and modification examples.

Furthermore, when image pickup means such as the simultaneous type endoscope 2A provided with the color filter 11a as in the first embodiment is adopted, a filter for allowing to pass white color light (in other words, visible wavelength band) may be disposed on the outer circumferential side of the rotation filter 25 and white color light that has passed through the filter may be irradiated onto the object to be examined in the normal observation mode.

In this case, for example, the signal separation circuit 33 in FIG. 1 can also generate image signals of R, G and B and store the image signals in the first frame memory 34a to the third frame memory 34c respectively.

The image signals of R, G and B stored in the first frame memory 34a to the third frame memory 34c may be subjected to pixel interpolation by the interpolation circuit 35, passed through the image processing circuit 36 and through the D/A conversion circuit 37, outputted to the R, G and B channels of the monitor 5 and a normal image may be displayed in color on the monitor 5 as in the aforementioned case.

Embodiments configured by partially combining the aforementioned respective embodiments also belong to the present invention.

What is claimed is:

1. A fluorescent imaging device comprising:
   an irradiation section that irradiates an object to be examined with excitation light and reference light;
   an image pickup section that picks up a fluorescence image based on the excitation light and a reflected light image including a first reflected light image of at least a predetermined wavelength region based on the reference light;
   an image signal generating section that generates a plurality of image signals making up a diagnostic fluorescent image including an image signal of a fluorescent image corresponding to the fluorescence image, an image signal of the reflected light image including a first reflected light image corresponding to the first reflected light image from the reflected light image;
   a comparison section that compares intensity of the image signal of the fluorescent image and that of the image signal of the reflected light image including the first reflected light image multiplied by a predetermined value, or compares a value obtained by calculating relative intensity between the fluorescent image and the first reflected light image based on the image signal of the fluorescent image and the image signal of the reflected light image including the first reflected light image, with a predetermined threshold; and
   a selection section that selectively outputs one of the image signal of the reflected light image including the first reflected light image and the image signal of the fluorescent image based on the comparison result by the comparison section as one image signal making up the diagnostic fluorescent image.

2. The fluorescent imaging device according to claim 1, wherein the reference light includes first reference light of a blue color wavelength band, and
   the image pickup section picks up the first reflected light image based on the first reference light.

3. The fluorescent imaging device according to claim 2, wherein the first reference light is light of a narrow band whose center wave length is set to a wavelength of 415 nm selectively absorbed by hemoglobin, and
   the image pickup section picks up the first reflected light image with reflected light from an object to be examined irradiated with the first reference light.

4. The fluorescent imaging device according to claim 2, wherein the image signal generating section generates an image signal of a fluorescent image corresponding to the fluorescence image picked up in a green color wavelength region.

5. The fluorescent imaging device according to claim 1, wherein the selection section assumes one of the image signal of the reflected light image including the first reflected light image and the image signal of the fluorescent image as one image signal making up the diagnostic fluorescent image based on the comparison result of the comparison section and outputs the image signal to a color display section as a specific color signal.

6. The fluorescent imaging device according to claim 1, wherein the predetermined threshold is set to a value to discriminate between a hyperplastic polyp as a normal region and an adenoma as a lesioned region in biological mucous membrane of the object to be examined.

7. The fluorescent imaging device according to claim 1, wherein when the image signal of the reflected light image including the first reflected light image is divided by the image signal of the fluorescent image and the relative intensity is set, the predetermined threshold is set to a value greater than 1.

8. The fluorescent imaging device according to claim 1, wherein the reference light includes second and third reference light of red color and green color narrow bands, and
   the image pickup section picks up the second and third reflected light images of a narrow band based on the second and third reference light.

9. The fluorescent imaging device according to claim 8, wherein the irradiation section switches between second and third reference light of the red color and green color narrow bands and fourth, fifth and sixth reference light of red color, green color and blue color wide bands as the reference light and can irradiate the reference light onto the object to be examined.

10. The fluorescent imaging device according to claim 8, wherein the image signal generating section further generates an average image signal resulting from averaging intensity of the second and third reflected light images, assumes the average image signal as a plurality of image signals making up the diagnostic fluorescent image and outputs the average image signal together with the one image signal to a color display section.

11. The fluorescent imaging device according to claim 1, wherein the image pickup section comprises a color filter that allows to pass each wavelength band of red color, green color and blue color and picks up two fluorescence images of each wavelength band of the red color and green color based on the excitation light.

12. The fluorescent imaging device according to claim 11, wherein the image signal generating section performs a calculation on the image signals of the two fluorescence images, assumes the fluorescence image signals generated as a plurality of image signals making up the diagnostic fluorescent image and outputs the fluorescence image signals together with the one image signal to a color display section.

13. An operation method of a fluorescent imaging device, comprising:

a first step of an image signal generating section generating a plurality of image signals making up a diagnostic fluorescent image which includes an image signal of a fluorescent image corresponding to the fluorescence image picked up by an image pickup section based on excitation light irradiated from an irradiation section onto an object to be examined, and an image signal of a reflected light image including a first reflected light image corresponding to the first reflected light image from the reflected light image including at least the first reflected light image picked up by the image pickup section based on reference light irradiated from the irradiation section onto the object to be examined;

a second step of a comparison section comparing intensity of the image signal of the fluorescent image with that of the image signal of the reflected light image including the first reflected light image multiplied by a predetermined value, or comparing a value obtained by calculating relative intensity between the fluorescent image and the first reflected light image based on the image signal of the fluorescent image and the image signal of the reflected light image including the first reflected light image, with a predetermined threshold; and a third step of a selection section selectively outputting any one of the image signal of the reflected light image including the first reflected light image and the image signal of the fluorescent image based on the comparison result as one image signal making up the diagnostic image.

14. The operation method of the fluorescent imaging device according to claim 13, wherein the reference light is light of a narrow band whose center wave length is set as a wavelength of 415 nm selectively absorbed by hemoglobin, and in the first step, the first reflected light image is picked up with reflected light from the object to be examined irradiated with the reference light.

15. The operation method of the fluorescent imaging device according to claim 13, wherein when the image signal of the reflected light image including the first reflected light image is divided by the image signal of the fluorescent image and the relative intensity is set, the predetermined threshold is set to a value greater than 1.

* * * * *